(12) United States Patent
Johnson et al.

(10) Patent No.: US 7,135,146 B2
(45) Date of Patent: Nov. 14, 2006

(54) UNIVERSAL NON-CONTACT DISPENSE PERIPHERAL APPARATUS AND METHOD FOR A PRIMARY LIQUID HANDLING DEVICE

(75) Inventors: James E. Johnson, Sebastopol, CA (US); Neil R. Picha, Petaluma, CA (US); David A. Martin, Santa Rosa, CA (US); Joel McComb, Portola Valley, CA (US)

(73) Assignee: Innovadyne Technologies, Inc., Santa Rosa, CA (US)

( * ) Notice: Subject to any disclaimer, the term of this patent is extended or adjusted under 35 U.S.C. 154(b) by 620 days.

(21) Appl. No.: 10/237,916

(22) Filed: Sep. 6, 2002

(65) Prior Publication Data

US 2003/0072679 A1    Apr. 17, 2003

Related U.S. Application Data

(63) Continuation-in-part of application No. 09/689,548, filed on Oct. 11, 2000, now Pat. No. 6,852,291.

(60) Provisional application No. 60/318,245, filed on Sep. 7, 2001.

(51) Int. Cl.
*B10L 3/02* (2006.01)
*G01N 1/02* (2006.01)

(52) U.S. Cl. .................. 422/100; 422/103; 422/63; 422/65; 422/67; 422/68.1; 73/863.25; 73/864; 73/864.01; 73/864.11

(58) Field of Classification Search .............. 422/100, 422/68.1, 62–67; 73/863.24, 863.25, 864, 73/864.01, 864.11
See application file for complete search history.

(56) References Cited

U.S. PATENT DOCUMENTS

| | | | |
|---|---|---|---|
| 3,405,734 A | 10/1968 | Smit et al. | |
| 3,645,142 A | 2/1972 | Turpin | |
| 3,747,630 A | 7/1973 | Hurrell | |
| 3,796,239 A | 3/1974 | Zindler et al. | |
| 3,868,970 A | 3/1975 | Ayers et al. | |
| 3,963,148 A | 6/1976 | Proni et al. | |
| 3,994,423 A | 11/1976 | Burg | |
| 4,013,413 A | 3/1977 | Stewart et al. | |
| 4,120,661 A | 10/1978 | Naono | |
| 4,369,664 A | 1/1983 | Bunce et al. | |
| 4,459,267 A | 7/1984 | Bunce et al. | |
| 4,461,328 A | 7/1984 | Kenney | |
| 4,623,008 A | 11/1986 | Shibata et al. | |
| 4,625,569 A | 12/1986 | Toei et al. | |
| 4,694,861 A | 9/1987 | Goodale et al. | |
| 4,702,889 A | 10/1987 | Cabrera et al. | |
| 4,705,627 A | 11/1987 | Miwa et al. | |
| 4,723,262 A | 2/1988 | Noda et al. | |
| 4,726,932 A | 2/1988 | Feier et al. | |
| 4,818,706 A | 4/1989 | Starr | |
| 4,948,565 A | 8/1990 | Bemis et al. | |
| 5,104,621 A * | 4/1992 | Pfost et al. .................. | 422/67 |
| 5,207,109 A | 5/1993 | Olsen | |
| 5,250,263 A | 10/1993 | Manz | |
| 5,312,757 A | 5/1994 | Matsuyama et al. | |
| 5,405,585 A | 4/1995 | Coassin | |
| 5,465,582 A | 11/1995 | Bliss et al. | |
| 5,525,515 A | 6/1996 | Blattner | |
| 5,544,535 A | 8/1996 | Thomas | |
| 5,578,275 A | 11/1996 | Rosenberg et al. | |
| 5,599,500 A * | 2/1997 | Jones .......................... | 422/62 |
| 5,601,115 A | 2/1997 | Broerman | |
| 5,743,960 A | 4/1998 | Tisone | |
| 5,763,278 A | 6/1998 | Sickinger et al. | |
| 5,820,824 A | 10/1998 | Tanaka | |
| 5,833,925 A | 11/1998 | Shu et al. | |
| 5,849,598 A | 12/1998 | Wilson et al. | |
| 5,906,795 A | 5/1999 | Nakashima et al. | |
| 5,915,284 A | 6/1999 | Meltzer et al. | |
| 5,955,373 A * | 9/1999 | Hutchins et al. .............. | 436/48 |
| 5,985,214 A | 11/1999 | Stylli et al. | |
| 6,033,911 A | 3/2000 | Schultz et al. | |
| 6,040,186 A | 3/2000 | Lewis et al. | |

| | | | |
|---|---|---|---|
| 6,045,755 A * | 4/2000 | Lebl et al. ................... | 422/65 |
| 6,063,339 A | 5/2000 | Tisone et al. | |
| 6,066,298 A | 5/2000 | Fukunaga | |
| 6,068,393 A * | 5/2000 | Hutchins et al. ............ | 700/112 |
| 6,083,763 A | 7/2000 | Balch | |
| 6,096,276 A | 8/2000 | Laursen | |
| 6,112,605 A | 9/2000 | Papen et al. | |
| 6,149,870 A | 11/2000 | Parce et al. | |
| 6,158,269 A | 12/2000 | Dorenkott et al. | |
| 6,182,719 B1 * | 2/2001 | Yahiro ....................... | 141/130 |
| 6,299,840 B1 * | 10/2001 | Watanabe et al. ............ | 422/63 |
| 6,322,752 B1 | 11/2001 | Siddiqui et al. | |
| 6,323,035 B1 * | 11/2001 | Kedar et al. ................. | 436/43 |
| 6,325,114 B1 * | 12/2001 | Bevirt et al. ................ | 141/130 |
| 6,372,185 B1 * | 4/2002 | Shumate et al. ............. | 422/10 |
| 6,378,556 B1 | 4/2002 | Fondse | |
| 6,432,365 B1 * | 8/2002 | Levin et al. ................ | 422/100 |
| 6,447,678 B1 | 9/2002 | Chau | |
| 6,503,454 B1 * | 1/2003 | Hadimioglu et al. ....... | 422/100 |
| 6,558,623 B1 * | 5/2003 | Ganz et al. .................. | 422/63 |
| 6,605,257 B1 * | 8/2003 | Nakazawa et al. ......... | 422/100 |
| 6,627,446 B1 * | 9/2003 | Roach et al. ................ | 436/43 |
| 6,730,517 B1 * | 5/2004 | Koster et al. ................ | 436/47 |
| 2001/0014477 A1 | 2/2001 | Pelc et al. | |
| 2001/0016177 A1 | 2/2001 | Pelc et al. | |
| 2001/0055814 A1 | 8/2001 | Sasaki | |
| 2001/0026772 A1 | 10/2001 | Fuerst et al. | |
| 2001/0053337 A1 | 12/2001 | Doktycz et al. | |
| 2001/0055545 A1 | 12/2001 | Takii et al. | |
| 2002/0012611 A1 * | 1/2002 | Stylli et al. ................... | 422/65 |
| 2002/0051737 A1 * | 5/2002 | Sollbohmer et al. ........ | 422/100 |
| 2002/0176801 A1 * | 11/2002 | Giebeler et al. ......... | 422/82.05 |
| 2002/0192113 A1 | 12/2002 | Uffenheimer et al. | |
| 2003/0017085 A1 * | 1/2003 | Kercso et al. .............. | 422/104 |
| 2003/0021734 A1 | 1/2003 | Van et al. | |
| 2003/0022380 A1 * | 1/2003 | Jakubowicz et al. ......... | 436/54 |
| 2003/0027345 A1 * | 2/2003 | Friswell et al. .............. | 436/49 |
| 2004/0014228 A1 * | 1/2004 | Brignac et al. .............. | 436/43 |
| 2004/0047765 A1 * | 3/2004 | Gordon et al. ................ | 422/63 |

FOREIGN PATENT DOCUMENTS

| | | |
|---|---|---|
| AU | A-33209/84 | 3/1985 |
| CA | 2 202 649 | 12/2000 |
| EP | 0 810 438 | 3/1997 |
| EP | 0 024 230 | 2/1998 |
| EP | 1197693 A2 | 4/2002 |
| EP | 1 334 770 | 1/2003 |
| FR | 1.428.878 | 2/1966 |
| WO | WO 97/26539 | 7/1997 |
| WO | WO 99/21031 | 4/1999 |
| WO | WO 99/30168 | 6/1999 |
| WO | WO 99/42752 | 8/1999 |
| WO | WO 00/51736 | 9/2000 |
| WO | WO 01/04909 | 1/2001 |
| WO | WO 01/28701 | 4/2001 |
| WO | WO 01/65214 | 9/2001 |

OTHER PUBLICATIONS

Patent Abstracts of Japan, Publication No. 63295267, *Recovering Method For Ink Jet Recorder*, Moriyama Jiro, filed May 27, 1987.
Patent Abstracts Of Japan, Application No. 2000142062, *Variable Discharge Capacity Liquid Dispensation Device*, Otawara Shigeki.
Hue P. Le, *Progress and Trends in Ink-jet Printing Technology*, Journal Of Imaging Science And Technology, vol. 42, No. 1, Jan./Feb. 1998, pp. 49-62.
Ilene Schneider, *Instrumentation—Doing More With Less—Discover the turnkey systems now streamlining teh entire liquid handling process*, Sep. 2002—*Geonomics & Proteomics*.
Patent Abstracts of Japan, Publication No. 63-295267, Recovering Method For Ink Jet Recorder, Tokunaga Tatsuyuki, et al., published Dec. 1, 1988, filed May 27, 1987.
European Search Report dated May 9, 2005 from related application No. 03704032.6

* cited by examiner

*Primary Examiner*—Brian R. Gordon
(74) *Attorney, Agent, or Firm*—Beyer Weaver & Thomas LLP

(57) ABSTRACT

A removable secondary liquid dispensing module for use with an existing, automated liquid handling system that defines a work area having a plurality of discrete work stations. Each of the work stations of the automated liquid handling system includes a lab ware site and alignment structure enabling the removable securing standardized microtiter-plates at respective lab ware site. A plate positioning mechanism is configured to move and position the microtiter plates to and from the lab ware sites of the respective work stations thereof and into engagement with the respective carrier alignment structure thereof. Further, a primary liquid dispensing device is configured for selective contact-type dispensing of discrete quantities of fluid, in the range of about one (1) microliter to about ten (10) milliliters, into the test sites of the microtiter plates secured in the respective alignment structure of the respective work station. The removable secondary liquid dispensing module includes a base member dimensioned to fit substantially within a footprint of a work station, and mounting hardware adapted to removably secure the base member in the work station. A support platform is affixed to the base member, and is configured to support a microtiter-plate. An alignment mechanism is configured to removably receive and secure the a microtiter-plate therein by the plate positioning mechanism of the automated liquid handling system. The support platform and alignment mechanism cooperate to form and provide a lab ware site suitable for secured receipt of a microtiter-plate. The secondary liquid dispensing module further includes a secondary liquid dispensing device which is self-contained and operationally independent from the primary liquid dispensing device. The secondary dispensing device is further adapted for selective non-contact-type dispensing of discrete quantities of fluid, in the range of about one (1) nanoliter to about ten (10) microliters, into the test sites of the microtiter-plate.

34 Claims, 27 Drawing Sheets

ASPIRATE POSITION

DISPENSE POSITION

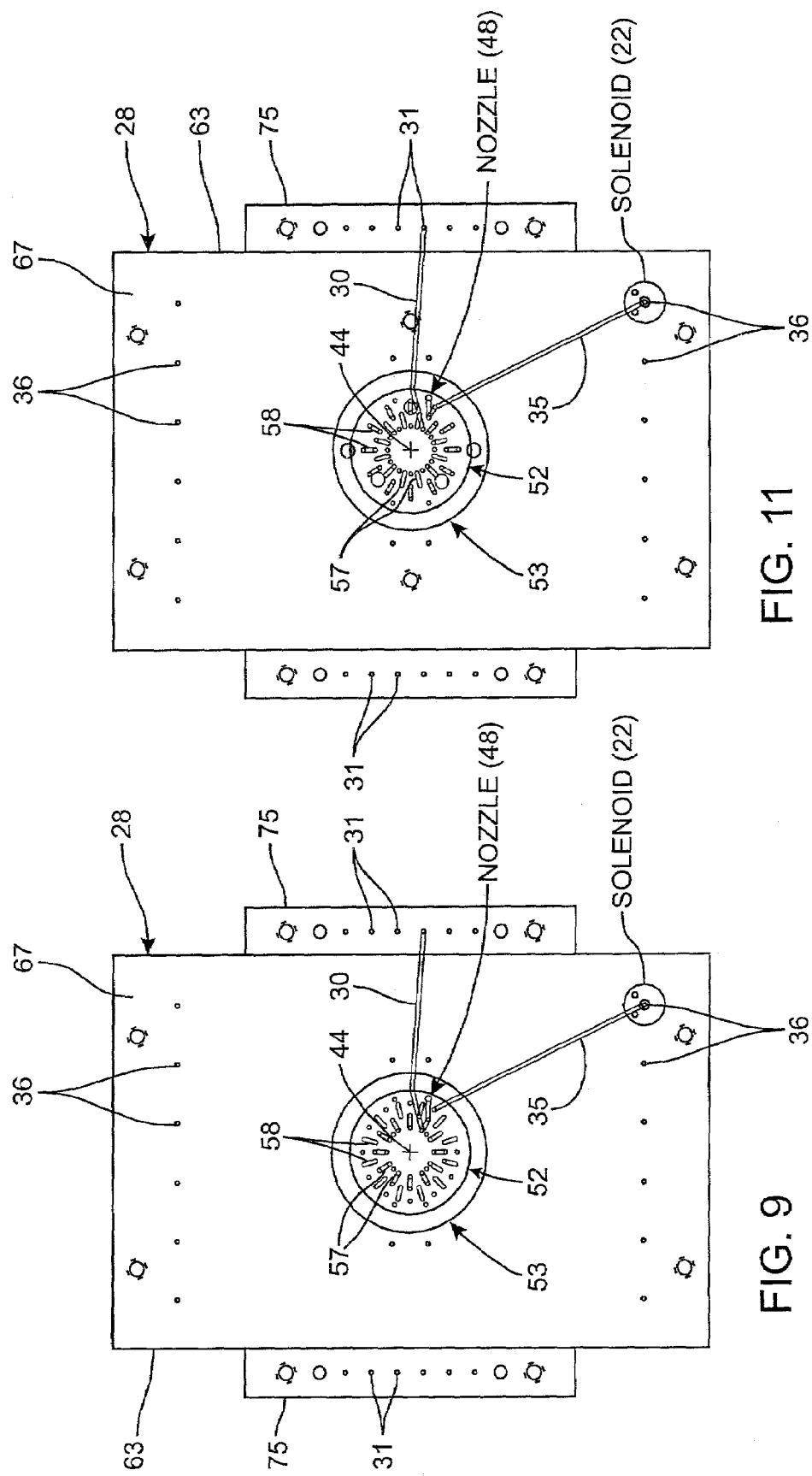

ASPIRATE POSITION

DISPENSE POSITION

ASPIRATE POSITION

DISPENSE POSITION

ASPIRATE POSITION

DISPENSE POSITION

UNIVERSAL NON-CONTACT DISPENSE PERIPHERAL APPARATUS AND METHOD FOR A PRIMARY LIQUID HANDLING DEVICE

RELATED APPLICATION DATA

This application is a continuation-in-part application based upon patent application Ser. No. 09/689,5548, naming Johnson et al. as inventors, filed Oct. 11, 2000, and entitled HYBRID VALVE APPARATUS AND METHOD FOR LIQUID HANDLING, the entirety of which is incorporated herein by reference in its entirety for all purposes.

The present application also claims priority under 35 U.S.C. §119 to U.S. Provisional Application Ser. No. 60/318,245, naming Johnson et al. inventors, and filed Sep. 7, 2001, and entitled UNIVERSAL NON-CONTACT DISPENSE PERIPHERAL FOR LIQUID HANDLING, the entirety of which is incorporated herein by reference in its entirety for all purposes.

TECHNICAL FIELD

The present invention relates to the field of sample analysis employing automated liquid handling systems and sample carriers, and more particularly, relates to methods and apparatus for increasing the fluid dispense capacity and versatility of existing liquid handling systems during large-scale chemical or biochemical screening assays, syntheses, arraying and plate spotting.

BACKGROUND ART

Advances in Life Sciences, particularly in genomics and proteomics, have greatly increased the potential number of reactions and analyses that must be performed by the biotechnology and pharmaceutical industries. An estimated 30 million tests are required to screen a typical pharmaceutical company's compound library against target receptors. The typical number of tests will increase dramatically as information is gleaned from the sequencing of the human genome. To meet these increasing throughput demands in an economically feasible manner, miniaturization of tests is imperative.

Technological advances are enabling the demonstration and use of microscale chemical/biochemical reactions for performing various types of analyses. Implementation of these reactions at such smaller scales offer economies that are unmatched by conventional approaches. Reduced volumes can lower costs by an order of magnitude but conventional liquid-handling devices fail at the required volumes. Parallel implementation provides even greater advantages as demonstrated by the use of high-density plates for screening and high-density MALDI-TOF plates for mass spectrometry analyses of proteins. The rate-limiting hardware is low volume liquid transfer technology that is robust and scalable for compounds of interest. With growing demand, the development of liquid handling devices adept at manipulating sub-microliter volumes (i.e., nanoliters to microliters) of multiple reagent is needed.

Most current systems for handling liquid reagents often employ a "pick and place" technique where a sample from a source plate, usually a microtiter plate, is picked up and placed into another reservoir known as the target plate. This technique is often applied for replicating plates, where scale reduction between the source and the target plates are beneficially realized. Typically, an appropriate volume is aspirated from a source plate and deposited to a target site on a multiple target plate. In this arrangement, reduced sample volumes and sample spacing are required for higher degrees of miniaturization.

However, many of these older conventional automated liquid handling systems currently in use for nucleic acid sequencing or other molecular biology procedures for therapeutic and research procedures such as DNA restriction mapping, DNA probe generation, DNA replication, DNA sample processing and cycle sequencing are designed to manipulate and dispense fluids in the microliters to milliliters range.

While these conventional liquid handling workstations are adequate for manipulating larger volume fluid dispensing for the particular applications which they address (e.g., about 1 µl to about 10 ml), they are not suitable for accurately delivering sub-microliter volume fluids (i.e., nanoliter to microliter) to perform the above-mentioned applications. Thus, it would be desirable to provide a secondary liquid dispensing system and method that cooperates with an existing, conventional primary liquid handling device to enable nanoliter to microliter dispensing of fluids, while maintaining the microliters to milliliters fluid dispensing of the primary liquid dispensing system

DISCLOSURE OF INVENTION

The present invention provides a removable secondary liquid dispensing module for use with an existing, automated liquid handling system defining a work area having a plurality of discrete work stations. Each of the work stations of the automated liquid handling system provides a lab ware site and alignment structure enabling the removable securing of standardized microtiter-plates at respective lab ware sites. Each microtiter or microwell plate includes a plurality of test or sample sites therein for sample analysis of a sample or other type of molecular biology procedures. The automated liquid handling system further includes a plate positioning mechanism and a primary liquid dispensing device. The plate positioning mechanism is configured to move and position the microtiter plates to and from the lab ware sites of the respective work stations thereof and into engagement with the respective carrier alignment structure thereof. The primary liquid dispensing device is configured for selective contact-type dispensing of discrete quantities of fluid, in the range of about one (1) microliter to about ten (10) milliliters, into the test sites of the microtiter plates secured in the respective alignment structure of the respective work station.

The removable secondary liquid dispensing module includes a base member dimensioned to fit substantially within a footprint of a work station, and mounting hardware adapted to removably secure the base member in the work station. A support platform is affixed to the base member, and is configured to support a microtiter-plate. An alignment mechanism is configured to removably receive and secure the microtiter-plate therein by the plate positioning mechanism of the automated liquid handling system. The support platform and alignment mechanism cooperate to form and provide a lab ware site suitable for secured receipt of a microtiter-plate. The secondary liquid dispensing module further includes a secondary liquid dispensing device which is operationally independent from the primary liquid dispensing device. The secondary dispensing device is further adapted for selective non-contact-type dispensing of discrete quantities of fluid, in the range of about one (1) nanoliter to about ten (10) microliters, into the test sites of the microtiter-plate.

Accordingly, the present invention provides a self-contained secondary liquid handling system that can be mounted within the footprint of the work station of an existing automated liquid handling systems that enables a more precise fluid dispensing into the sample carrier test sites than that of the primary liquid handling system upon which it resides. For example, the liquid handling of coarser discrete quantities of fluid in the range of about one (1) microliter to about ten (10) milliliters may still be retained by the coarser primary liquid dispensing device by. However, when it is desirable to dispense smaller discrete quantities of fluid, in the range of about one (1) nanoliter to about ten (10) microliters, which these existing primary liquid dispensing systems are not designed, the more refined and accurate secondary liquid handling system may be utilized.

In one specific embodiment, the carrier alignment mechanism and the support platform cooperate to provide a Society of Bimolecular Screening (SBS) standard microtiter-plate lab ware site. Thus, the secondary liquid handling system of the present invention can then be operationally positioned into existing liquid handling systems which conform to the SBS standard, and function in cooperation therewith to improve the collective fluid capacity of the system.

Yet another embodiment discloses the secondary liquid handling system of the present invention with a fluid control component adapted to aspirate fluids therein from a fluid reservoir, and to dispense fluids therefrom, and a motion control component having a plurality of non-contact dispense nozzles fluidly coupled to the fluid control component to selectively dispense the aspirated fluids into selected targeted test sites of the microtiter-plate. An operation interface component is further coupled between the fluid control component and the motion control component for stand-alone or remote control operation of the fluid control component and the motion control component.

In another configuration, the fluid control component includes a hybrid valve apparatus that enables fluid aspiration, fluid dispensing and fluid switching to transfer fluid from one or more fluid reservoirs, and through selected non-contact dispense nozzles to the targeted test sites of the microtiter-plate. The fluid control component further includes an aspiration source in fluid communication with a first aspiration port of the hybrid valve apparatus, and a dispensing source in fluid communication with a first dispensing port of the hybrid valve apparatus. The hybrid valve apparatus includes a valve assembly, movable between an aspiration condition and a dispensing condition, and a manifold device, providing a fluid aspiration conduit having in fluid communication with the aspiration source through the first aspiration port thereof, and a second aspiration port in selective fluid communication with the valve assembly to selectively aspirate a liquid sample slug from the reservoir into a discrete sample path when the valve assembly is in the aspiration condition. The manifold device further provides a fluid dispensing conduit in fluid communication with the dispensing source through the first dispensing port thereof, and a second dispensing port in selective fluid communication with the valve assembly to selectively dispense at least one droplet of the liquid sample slug from the sample path when the valve assembly is in the dispensing condition. In the aspiration condition, the sample path is out of fluid communication with the dispensing source while, in the dispensing condition, the sample path is out of fluid communication with the aspiration source.

In one embodiment, the hybrid valve includes a plurality of aspiration actuators and a plurality of dispensing actuators to transfer fluid from a plurality of fluid reservoirs to a plurality of test sites on the substrate surface. The manifold device defines a plurality of independent fluid aspiration conduits, each of which includes a first aspiration port in fluid communication with a corresponding one of the plurality of aspiration actuators, and a second aspiration port terminating at a stator face of the manifold for selective fluid communication with the valve assembly. Thus, when the valve assembly is in the aspiration condition, each aspiration actuator can be operated to selectively aspirate a respective liquid sample slug from a corresponding reservoir of sample fluid into discrete sample paths. The manifold device further defines a plurality of fluid dispensing conduits, each having a respective first dispensing port in fluid communication with a corresponding one of the plurality of dispensing actuators, and a second dispensing port terminating at the stator face. When the valve assembly is in the dispensing condition, each dispensing actuator can be operated to selectively dispense at least one droplet of the corresponding liquid sample slug from the corresponding sample path.

Accordingly, at no time are the aspiration actuator or the dispensing actuator both in fluid communication with the sample path when the valve assembly is in either the aspiration or dispensing condition. This arrangement is highly beneficial in that contamination of the dispensing actuators can be eliminated by isolating the aspiration paths and dispensing actuators. Moreover, each fluid path is operatively switched between the aspiration actuator and the dispensing actuator enabling the use of conventional liquid handling techniques, such as air gaps, to isolate system hydraulic fluid during aspiration, and the subsequent low-volume, non-contact dispensing of the reagents or sample fluid to the test site.

In yet another specific embodiment, the motion control component includes a base member supporting the support platform thereon such that when the base member is strategically positioned at the discrete work station, the respective carrier alignment structure removably receives and secures the microtiter-plate therein at the respective discrete position. The motion control component further includes a motion controller device movably mounted to the base member for movement of the plurality of non-contact dispense nozzles above the mounted microtiter-plate for the selective dispense of the discrete quantities of fluid into the targeted test sites. The motion controller device includes a control post configured for movement along a three-axis X-Y-Z Cartesian coordinate system.

In another aspect of the present invention, a universal liquid handling system is provided to dispense fluids into the test sites of one or more sample carriers comprising a work area having a plurality of discrete work stations for performing lab work, and carrier alignment structure at one or more work stations configured to removably receive and secure one of the sample carrier at a respective discrete position therein. A frame assembly is positioned about the work area, and a movable support system is movably coupled to the frame assembly. The support system includes a sample carrier positioning mechanism and a first liquid dispensing device. The carrier positioning mechanism is configured to move and position the one or more sample carriers to and from the respective discrete position of the respective work station, and into and out of engagement with the respective carrier alignment structure thereof. The first liquid dispensing device is configured to selectively dispense discrete quantities of fluid, in the range of about one (1) microliter to about ten (10) milliliters into the test sites of the one or more sample carriers secured in the respective alignment structure of the respective work station. The liquid handling system further includes a removable second liquid dispensing peripheral system adapted to be positioned within the work area at at least one of the discrete work stations. The second liquid dispensing peripheral system includes a support platform having respective carrier alignment structure to removably receive and secure sample carriers therein by the sample carrier positioning mechanism at the respective discrete position of the work station. The second liquid dispensing peripheral system is further operationally independent of the first liquid dispensing device and is adapted to selectively dispense discrete quantities of fluid, in the range of about one (1) nanoliter to about ten (10) microliters, into the test sites of sample carrier positioned therein.

In one specific arrangement, the sample carrier is provided by standardized microtiter-plates, and the carrier alignment structure is adapted to receive and secure the standardized microtiter-plates. In another configuration, the work stations conform to the specifications of a Society of Bimolecular Screening (SBS) lab ware site, and the second liquid dispensing peripheral system itself includes an SBS lab ware site integrated therewith so that when the peripheral system is mounted to the work station, a standard SBS lab ware site is provided for receipt of the sample carrier from the positioning mechanism there.

In still another specific embodiment, the first liquid dispensing device is a contact-type liquid dispenser, while the second liquid dispensing peripheral system is a non-contact-type liquid dispenser.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

FIG. 9 is a top plan view of the manifold device with the rotor face superimposed over the stator face at a rotor/stator interface in the aspiration condition.

FIG. 11 is a top plan view of the manifold device of FIG. 9 in the dispensing condition.

BEST MODE OF CARRYING OUT THE INVENTION

Figure 1:
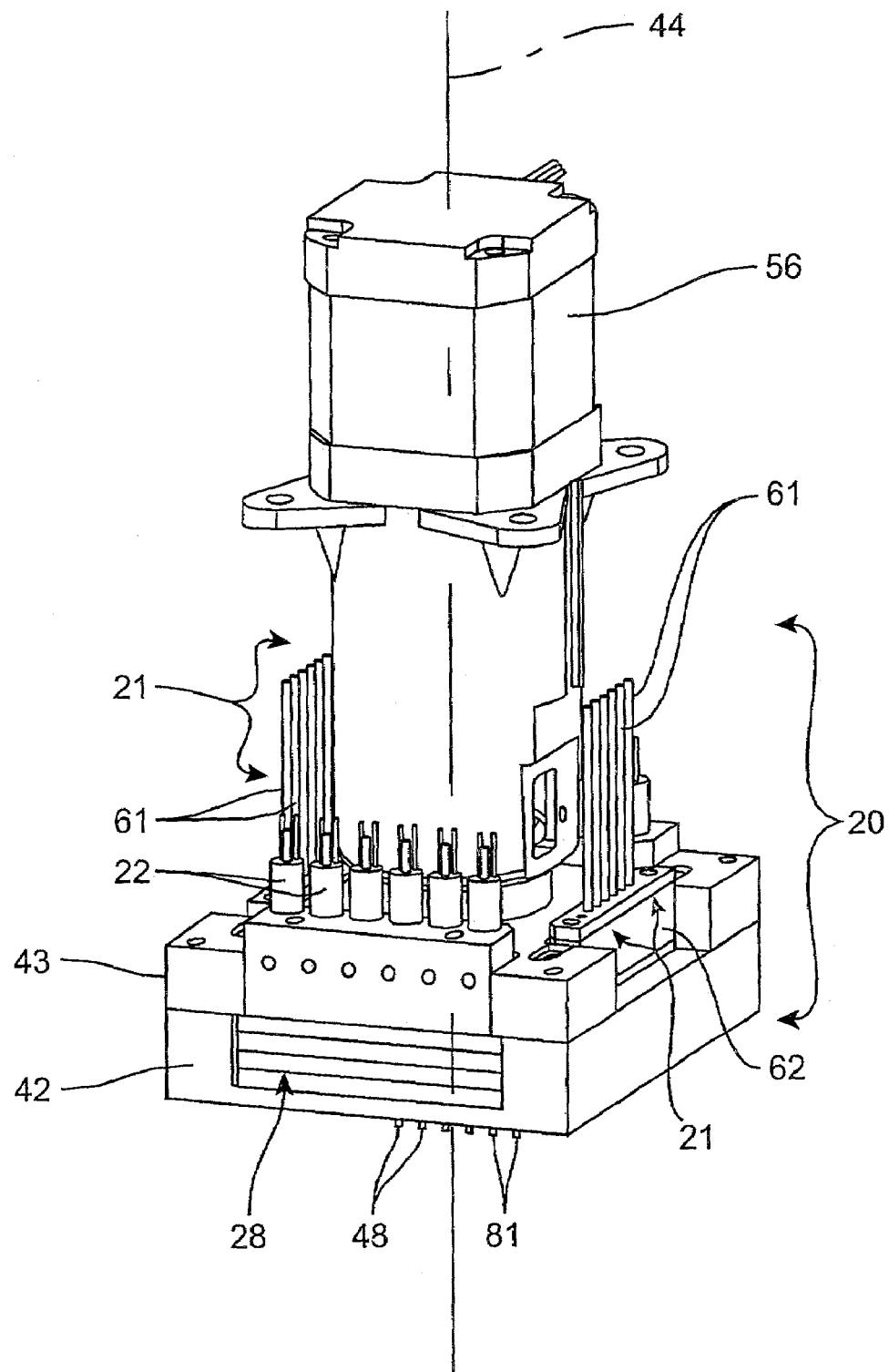
FIG. 1 is a top perspective view of the hybrid valve apparatus constructed in accordance with the present invention.

While the present invention will be described with reference to a few specific embodiments the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Referring now to FIGS. 1–6, 15 and 16, a hybrid valve apparatus, generally designated 20, is provided for use with an aspiration source 21 and a dispensing source 22 to transfer sample or reagent fluid from a reservoir 23 to a test site 25 on a substrate surface 26. Broadly, the hybrid valve apparatus 20 includes a valve assembly 27 (FIGS. 15 and 16) movable between an aspiration condition (FIGS. 5, 9 and 10) and a dispensing condition (FIGS. 6, 11 and 12), and a manifold device 28 coupled to the valve assembly. The manifold device 28 includes a fluid aspiration conduit 30 having a first aspiration port 31 in fluid communication with the aspiration source 21. On an opposite end of the aspiration conduit 30 is a second aspiration port 32 in selective fluid communication with the valve assembly 27 to selectively aspirate a liquid sample slug from the reservoir 23 into a discrete sample path 33 when the valve assembly 27 is in the aspiration condition. The manifold device 28 further includes a fluid dispensing conduit 35 having a first dispensing port 36 in fluid communication with the dispensing source 22, and a second dispensing port 37 in selective fluid communication with the valve assembly 27. When the valve assembly 27 is oriented in the dispensing condition (FIGS. 6, 11 and 12), the sample path 33 is fluidly coupled to the dispensing source 22 to selectively dispense at least one droplet 34 of the liquid sample slug therefrom. Importantly, in this orientation, the valve assembly 27 also fluidly decouples the sample path 33 from the aspiration source 21. In contrast, in the aspiration condition (FIGS. 5, 9 and 10), the valve assembly 27 fluidly couples the sample path 33 to the aspiration source 21, while simultaneously being out of fluid communication with the dispensing source 22.

Accordingly, the hybrid valve apparatus provides a switching system which regulates fluid communication of the aspiration actuator and the dispensing actuator with the sample path containing the sample or reagent fluid. Whether the hybrid valve apparatus is in the aspiration condition or the dispensing condition, at no time will the valve assembly allow the sample path be in fluid communication with both the aspiration actuator and the dispensing actuator, simultaneously. This arrangement is beneficial in that the dispensing source can not be contaminated by the sampled fluid due to the isolating of the dispensing source from the sample path during the aspiration of the fluid into the sample path. Moreover, each sample path is operatively switched between the aspiration actuator and the dispensing actuator enabling the micro-metered, non-contact parallel distribution of the reagents or sample fluid to the test site.

Figure 3:
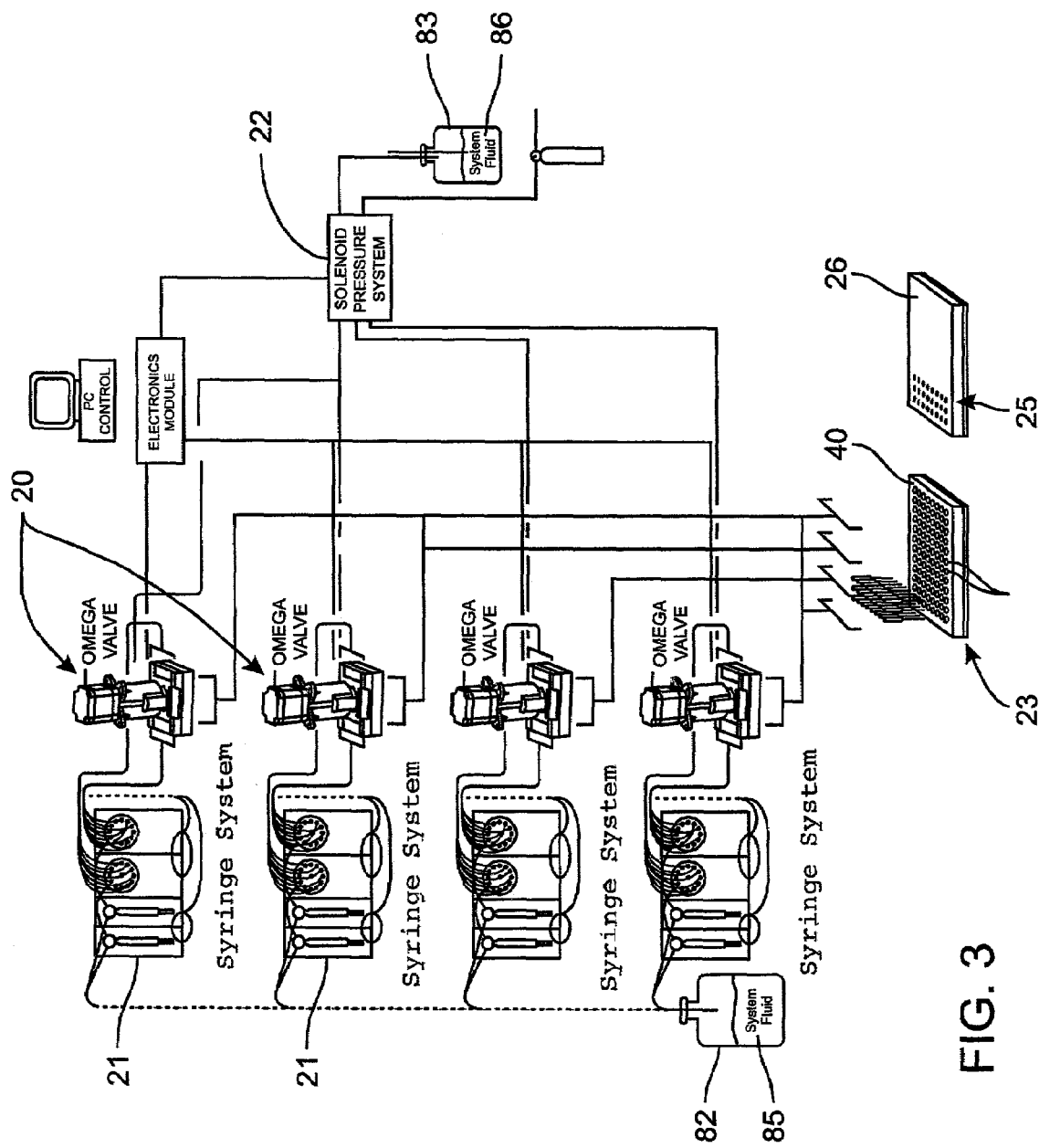
FIG. 3 is a schematic illustration of an assembly incorporating the hybrid valve apparatus of FIG. 1.

As best viewed in the schematic representation of FIG. 3, the present invention is particularly suitable for transferring chemical or biochemical samples or reagents from an array of reservoir wells 38 of a conventional microtiter plate 40, i.e. 96 or 384 wells, to an array of higher-density test sites 25, i.e. a 1536-well microtiter plate, or for fabrication of a chip-based biological sensor (commonly referred to as a "microarray") used for performing gene expression or other screening experiments. Briefly, the hybrid valve apparatus is adaptable for printing arrays wherein the distance between adjacent test sites 25, or test site pitch, is in the range of about 1 micron ($\mu m$) to about 10,000 microns ($\mu m$).

Thus, in the preferred embodiment, the manifold device 28 includes a plurality of fluid aspiration conduits 30, corresponding fluid dispensing conduits 35 and corresponding sample paths 33, which cooperate for the parallel transfer of fluid from the fluid reservoir 23 to the corresponding test sites 25 (FIGS. 3, 4, 13 and 14). Briefly, each fluid aspiration conduit 30 includes a first aspiration port 31 in fluid communication with a corresponding aspiration source or actuator, and an opposite second aspiration port 32 terminating at a stator face surface 41 of the manifold device 28. Moreover, each fluid dispensing conduit 35 includes a first dispensing port 36 in fluid communication with a corresponding dispensing actuator 22, and an opposite second dispensing port 37 also terminating at the manifold stator face 41 as well.

When oriented in the aspiration condition (FIGS. 5, 9 and 10), the valve actuator assembly 27 permits selective fluid communication of the sample paths 33 with the corresponding second aspiration ports 32 of the aspiration conduits 30 at the stator face 41, while simultaneously preventing fluid communication with the corresponding second dispensing ports 37 of the dispensing conduits 35. Conversely, when the valve assembly is oriented in the dispensing condition (FIGS. 6, 11 and 12), the sample paths 33 are moved into selective fluid communication with the corresponding second dispensing ports 37 at the stator face, while simultaneously being moved out of fluid communication with the second aspiration ports 32.

Preferably, the present invention includes twelve (12) independent aspiration conduits 30, and dispensing conduits 35 communicating with corresponding sample paths 33. Thus, inherently, the hybrid valve apparatus 20 may simultaneously deliver sample or reagent fluid to twelve test sites. Other configurations, containing greater of lesser number of independent conduits are possible. It will be appreciated, however, that the system can be configured for a one-to-one transfer of fluid, i.e., from each reagent reservoir to a designated test site. Such flexibility also lends itself to numerous variations of the preferred use. In particular, the hybrid valve apparatus can be configured for transferring sample or reagent fluids from a given number of reservoirs to a different number of test sites. For instance, the switching technology of the hybrid valve manifold device 28 can be designed such that fluid samples from multiple aspiration reservoirs 23 are dispensed on a single test site. Conversely, this, manifolding can be adapted for depositing fluid from a single reservoir 23 to multiple test sites.

Figure 2:
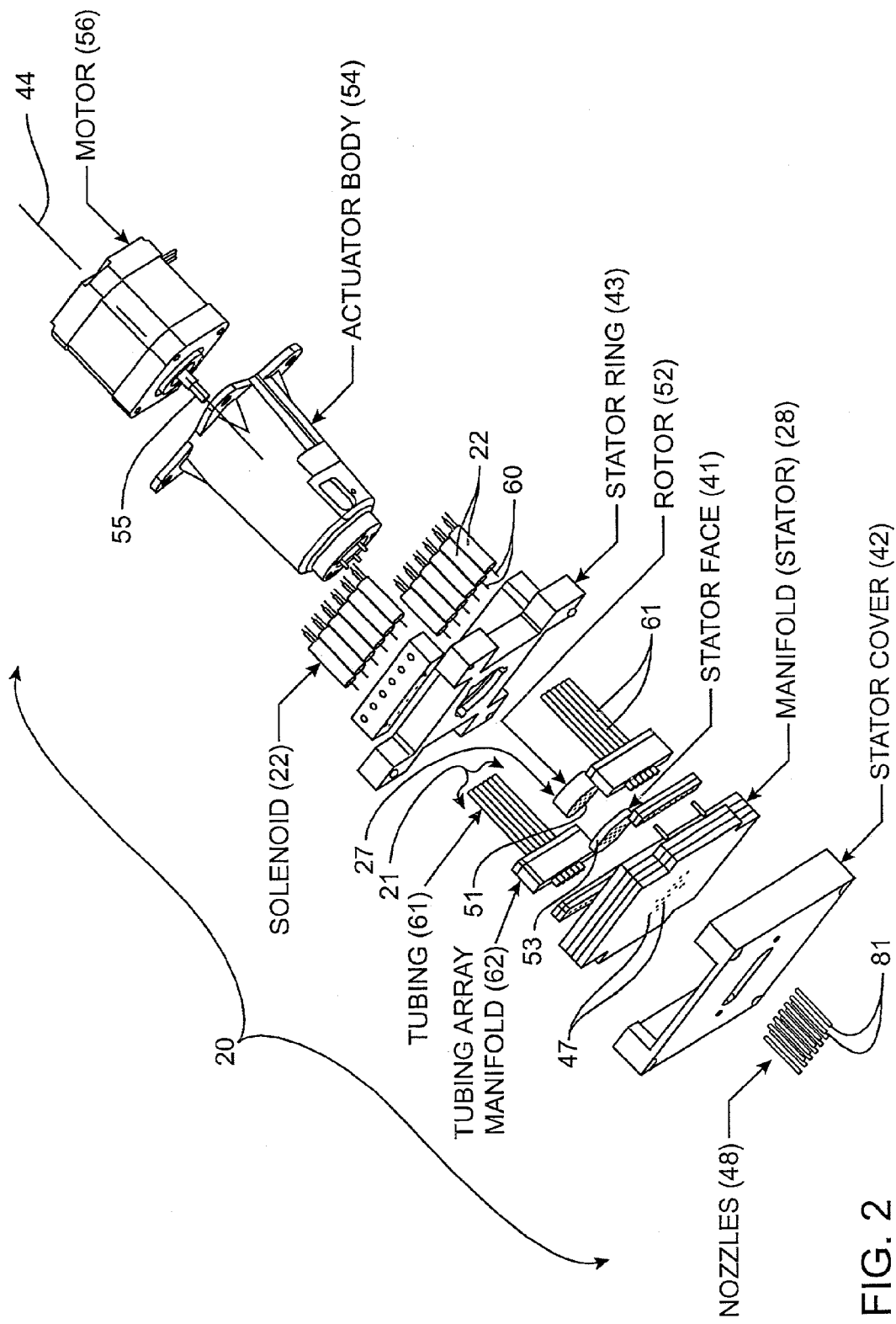
FIG. 2 is an exploded top perspective view of the hybrid valve apparatus of FIG. 1.

Briefly, as shown in FIGS. 1 and 2, the manifold device 28 is preferably sandwiched between a lower stator cover 42 and an upper stator ring 43 for stable support thereof. This assembly cooperates with a track or transport mechanism (not shown) which effects the relative movement between manifold device 28, the fluid reservoirs 23 and the test sites 25 (FIGS. 1 and 3). Preferably, the entire hybrid valve apparatus 20 is transported between the microtiter plates 40 and the array of test sites 25.

Although the hybrid valve apparatus 20 is adapted for simultaneously transferring multiple volumes of fluid sample or reagent to multiple chip test sites, a better understanding of the invention can be gained through a description of the operation thereof with respect to the transfer of the fluids from a single sample path 33 in the manifold device 28. In this description, briefly, the aspiration actuator 21 will be fluidly coupled to the manifold sample path 33, via the valve assembly 27, to aspirate sample fluid from the single reservoir 23 into the sample path. Subsequently, the sample path 33 will be switched, in fluid communication, to the dispensing conduit 35 for finely controlled dispensing of the sample fluid contained in the sample path 33. Accordingly, FIGS. 5, 6 and 9–12 intentionally depict a single set of fluid transfer elements.

Referring back to FIGS. 5 and 6, in this embodiment, each sample path 33 includes a primary passage portion 45 thereof defined by the manifold device 28. This primary passage portion 45 extends substantially vertically therethrough in a direction substantially parallel to an axis 44 of the hybrid valve apparatus 20. Further, each primary passage 45 includes an upper communication port 46 terminating at the stator face 41, and a lower communication port 47.

Figure 5:
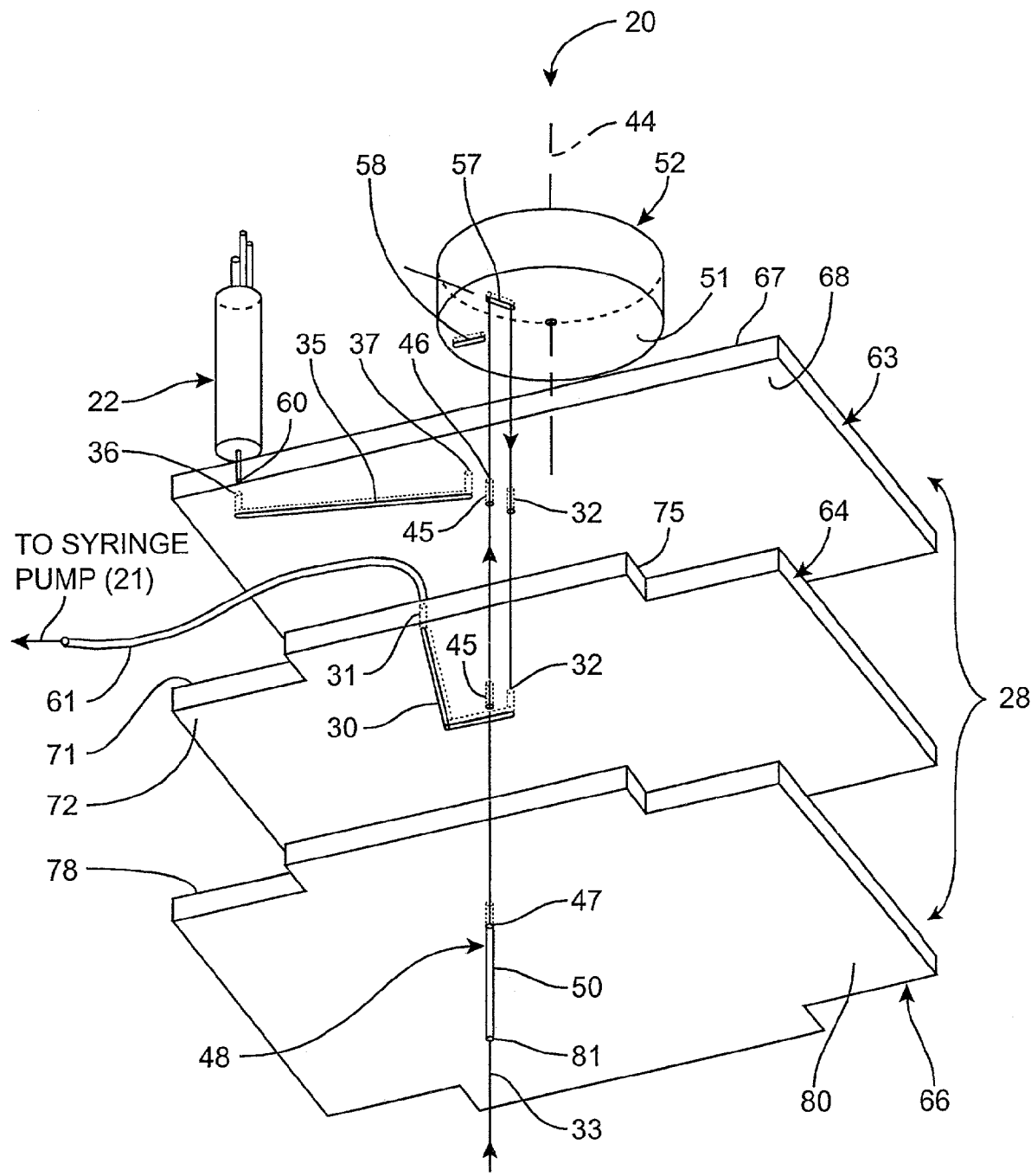
FIG. 5 is an enlarged, exploded bottom perspective view of one fluid path of the hybrid valve apparatus in the aspiration condition.
Figure 6:
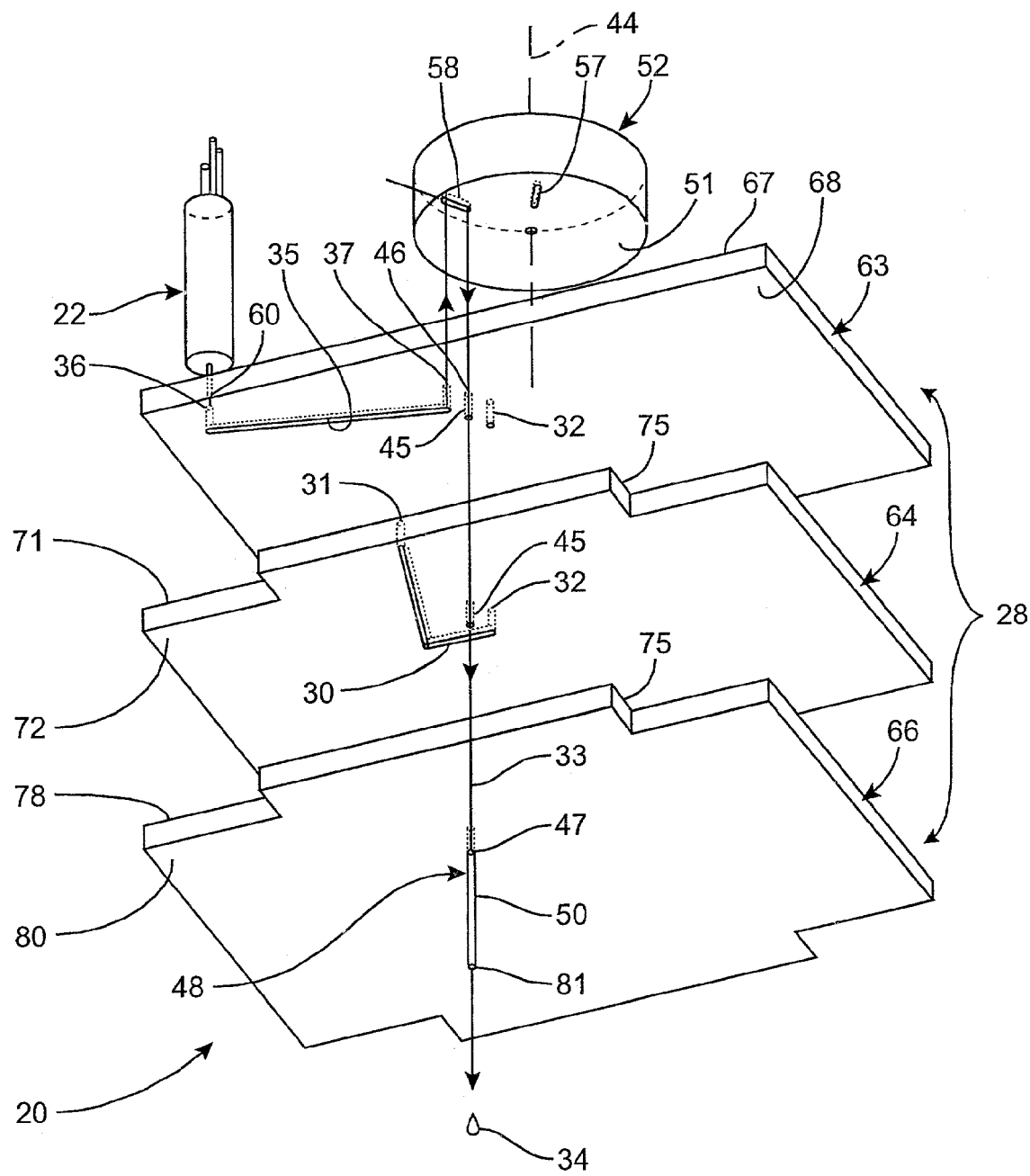
FIG. 6 is an enlarged, exploded bottom perspective view of one fluid path of the hybrid valve apparatus in the dispensing condition.

Preferably, as best illustrated in FIGS. 5 and 6, each primary passage 45 includes a corresponding nozzle member 48 extending outwardly from one of the lower communication ports 47. As will be described in greater detail below, each nozzle member is removably mounted to the manifold device 28 which enables individual aspiration of the sample fluid therein (in the aspiration condition) or individual dispensing of the sample fluid therefrom (in the dispensing condition). Moreover, a nozzle passage 50 extends longitudinally through the nozzle member 48 which inherently increases the volumetric capacity of the corresponding sample path 33.

Figure 8:
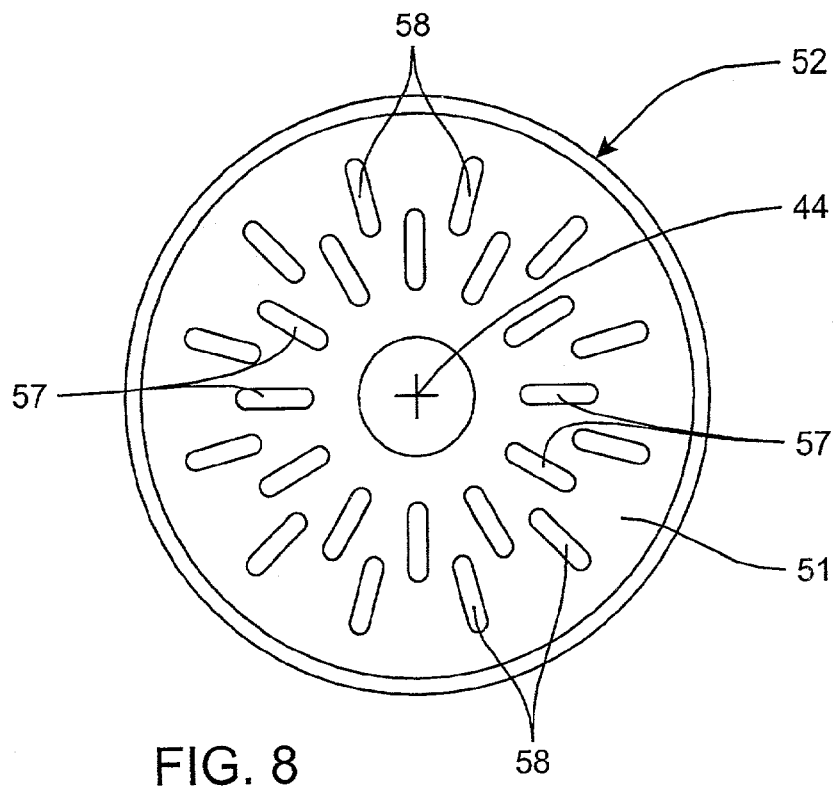
FIG. 8 is an enlarged, bottom plan view of a rotor face of a rotor element of the valve assembly.
Figure 7:
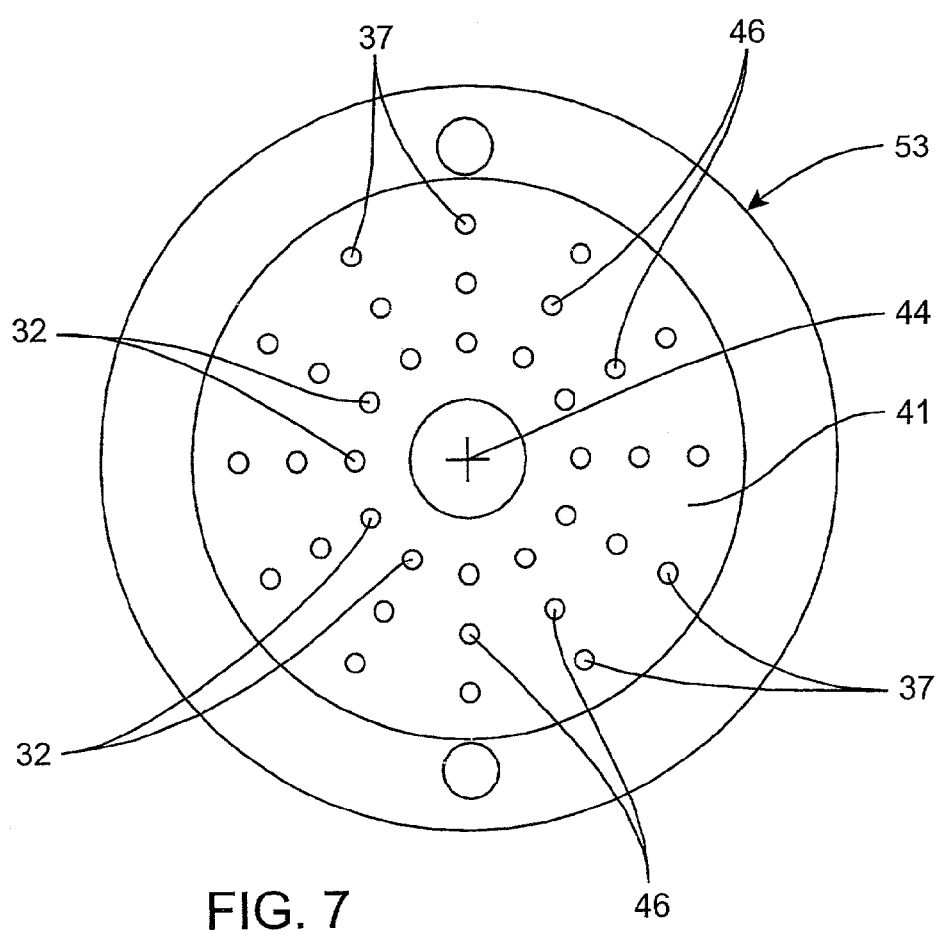
FIG. 7 is an enlarged, top plan view of a stator face of a stator element of the manifold device.

In accordance with the present invention, each of the aspiration conduits 30, the dispensing conduits 35 and the primary passages 45 include a respective port 32, 37 and 46 which terminates at the stator face 41 (FIG. 7) for fluid communication with a rotor face 51 of a rotor element 52 of the valve assembly (FIG. 8). In the preferred embodiment, each of the upper communication ports 46 of the primary passages 45 are equidistant from one another and are radially spaced about a rotational axis of the rotor element 52. Similarly, each of the second aspiration ports 32 and each of the second dispensing ports 37 is also equidistant from one another and radially spaced about the rotational axis 44. FIG. 7 best illustrates, however, that each of the second aspiration ports 32, which incidentally permit fluid communication with the corresponding aspiration actuator 21, are positioned at a radius from the rotation axis 44 smaller than that of the upper communication ports 46, while each of the second dispensing ports 37 are positioned at a radius larger than that of the upper communication ports. Finally, the upper communication ports 46, their corresponding second aspiration ports 32 and dispensing ports 37 are preferably collinearly aligned with a radial line intersecting the rotational axis 44.

It will be appreciated, however, that the corresponding ports can be alternatively spaced and oriented without departing from the true spirit and nature of the present invention. For example, while the collinear alignment between the corresponding ports 32, 37 and 46 is preferred, it is not a requirement for functionality of the manifold device, as will be apparent. Further, whether the second dispensing ports 37 and the second aspiration ports 32 are at a radial distance less than or greater than the radial distance of the upper communication ports 46 of the primary passages 45 from the rotational axis 44 is not determinative.

In accordance with the present invention, the valve assembly 27 and manifold device 28 are particularly suitable to the application of shear valve or flat face valve technology even though a rotary plug, a bank of 3-way solenoid valves, or MEMS device could be used. Thus, turning now to FIGS. 2, 5, 6 and 8, the valve assembly 27 is illustrated having rotor element 52 which provides the contact or rotor face 51 in opposed sliding contact with the stator face 41 at a rotor-stator interface. This high pressure sliding contact between the stator face 41 and the rotor face 51 provide a selective switching function between each of the sample paths 33 (i.e., the primary passage 45 and nozzle passage 50) and the corresponding aspiration actuators 21 or dispensing actuators 22, depending upon whether the rotor element 52 of the valve assembly 27 is in the aspiration condition or the dispensing condition.

Briefly, both the rotor element 52 and the stator face element 53 are composed of conventional shear valve or flat face valve materials which are adapted to support the high pressure contact at the stator-rotor interface. Typical of these materials include ceramic and synthetic composition, many of which are proprietary in nature. The rotor element 52 is rotatably mounted to a shaft which in turn is connected to a gear reduction inside the actuator body 54. The gear reduction is then coupled to the motor shaft 55 of a conventional electric motor 56 applied in shear valve or flat face valve technology.

As best shown in FIG. 8, the rotor element 52 of the valve assembly 27 provides a plurality of spaced-apart aspiration channels 57 and dispensing channels 58 which are slotted in the substantially planar rotor face 51 thereof. Each aspiration channel 57 and each dispensing channel 58 is elongated in shape, and extends generally along a radial line intersecting the rotational axis 44 of the rotor face 51. Further, the aspiration channels 57 and the dispensing channels 58 are equally spaced and are oriented in an alternating manner, relative one another. Accordingly, at the rotor-stator interface (i.e., the high pressure sliding contact between the stator face 41 and the rotor face 51), the rotor element 52 either reciprocates or rotates in one direction clockwise or counter clockwise to orient the valve assembly in the aspiration condition or the dispensing condition.

Figure 10:
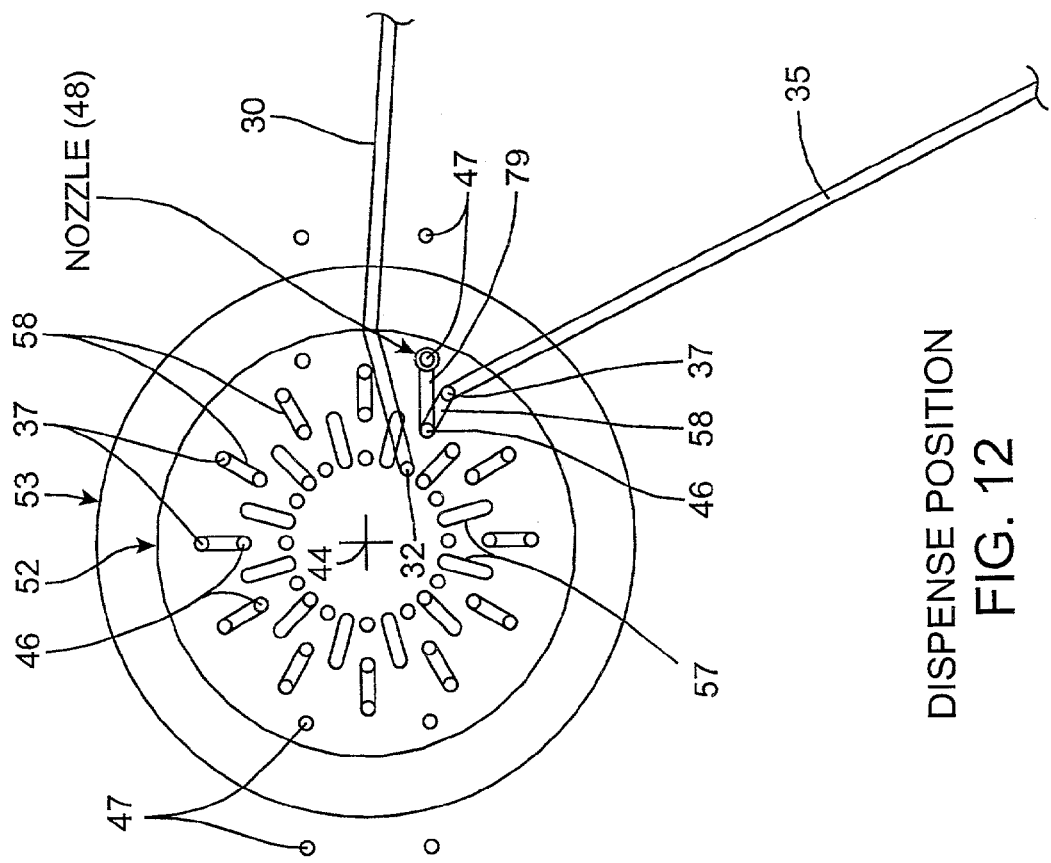
FIG. 10 is an enlarged top plan view of the rotor/stator interface of FIG. 9, in the aspiration condition.

When the rotor element 52 rotates about the rotational axis 44 to the aspiration condition, the aspiration channels 57 slotted into the rotor face 51 are rotated into alignment with the corresponding upper communication port 46 of the primary passages 45 and the second aspiration ports 32 of the aspiration conduits 30 of the stator face 41 to provide a fluid communication path therebetween (FIGS. 5, 9 and 10). Consequently, a fluid path is created by the aspiration channel 57 between the corresponding sample path 33 and the corresponding aspiration actuator 21. This permits selective aspiration of the fluid sample or reagent, via the aspiration actuator 21, from the sample reservoir 23 into the sample path 33 through the nozzle member. Simultaneously, in the aspiration condition, the second dispensing ports 37 of the dispensing conduits 35 are dead-ended into the rotor face 51 of the rotor element 52. Thus, the dispensing actuators 22 are out of fluid communication with the corresponding sample paths 33.

Figure 12:
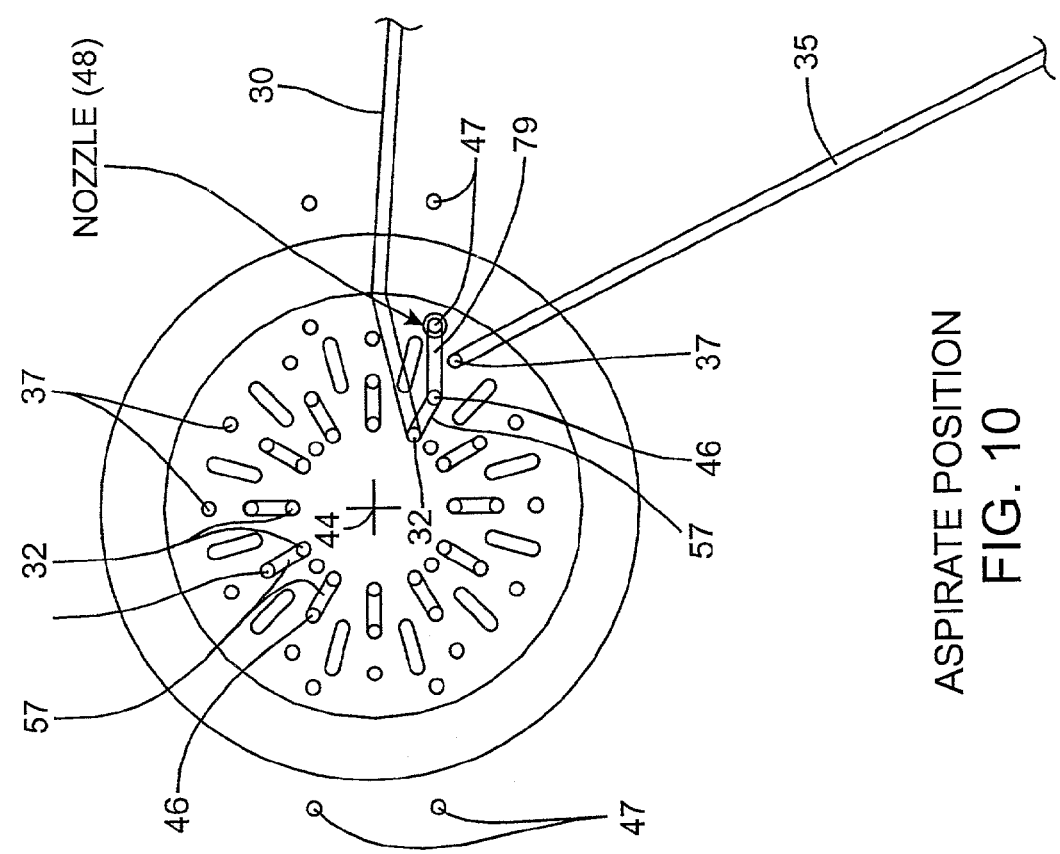
FIG. 12 is an enlarged top plan view of the rotor/stator interface of FIG. 11, in the dispensing condition.

Subsequently, as FIGS. 6, 11 and 12 illustrates, the rotor element 52 can be selectively rotated about rotational axis 44 to the dispensing condition. The radially extending dispensing channels 58, also slotted into the rotor face 51, are consequently rotated into collinear alignment with the corresponding upper communication ports 46 and the second dispensing ports 37 of the dispensing conduits 35 to provide a fluid communication path therebetween. The dispensing channels 58, thus, complete the fluid path between the corresponding sample path 33 and the corresponding dispensing actuator 22 to permit selective dispensing, via the dispensing actuator 22, of the fluid sample or reagent contained in the respective sample path 33. Similarly, in the dispensing condition, the second aspiration ports 32 of the dispensing conduits 35 are dead-ended into the rotor face 51 of the rotor element 52. Thus, the aspiration actuators 21 are out of fluid communication with their corresponding sample paths 33. Further, it will be appreciated that all twelve, or any number of, sample paths 33 can be simultaneously aspirated or dispensed.

Accordingly, the shear valve and manifold device arrangement of the present invention provides an accurate switching functionality between the aspiration actuators and the dispensing actuators. As above-indicated, such switching capability is beneficial in that the full potential of the high speed, precision ink-jet style dispensing actuators can be exploited to dispense the sample fluids or reagents from the sample paths. Moreover, the modular parallelism of system facilitates fabrication of non-contact devices, e.g. 24, 48, 96-tip, suitable to the expanding needs of the market.

It will be understood that while the valving functionality of the present invention is particularly adaptable for flat face or shear valves, other valve technologies are suitable such as solenoid valves, pinch valves and micro-machined valves, actuated by mechanical, electrical or pneumatic means.

Moreover, each dispensing conduit 35 includes an independent dispensing source 22 fluidly coupled to its corresponding first dispensing port 36 thereof. As best illustrated in FIGS. 1 and 2, the dispensing actuators 22 are preferably mounted to a corresponding dispensing actuator manifold device 28. These two opposed dispensing actuator manifolds separate and align the individual dispensing actuators into two sets of six actuators releasably mounted to the stator manifold device 28 as a unit. Each dispensing actuator 22 includes a delivery orifice 60 which is fluidly coupled to a corresponding first dispensing port 36 of the dispensing conduit 35.

In the preferred embodiment, each dispensing actuator 22 typically delivers a metered pressure pulse using a pressure ranging from about $6.9(10)^3$ N/m$^2$ to about $138(10)^3$ N/m$^2$, and having a duration ranging from about $(10)^{-6}$ seconds to about 10 seconds. Preferably, the dispensing actuator 22 is provided by a conventional ink-jet style printing valve or pump designed for drop-on-demand printing. Ink-jet style printing valves/pumps for drop-on-demand printing, including thermal, solenoid and piezoelectric types, are commercially available and well known in the art. For instance, the Lee Company of Essex, Conn. manufactures a solenoid-based ink-jet valve (Model No. INKX0502600AB) which is suitable for use with the present invention. Alternatively, conventional syringe pumps may be employed for metering as well.

The incorporation of ink-jet drop-on-demand printing technology into the dispense assembly of the present invention provides significant advantages vis-a-vis known systems for printing microarrays. In particular, the ability to deliver independent, short-duration, pressure pulses associated with ink-jet print valves enables the non-contact tunable delivery of reagent sample volumes in the range of about $(10)^{10}$ to about $(10)^{-12}$ liters. Upon application of a pressure pulse, at least one droplet of sample or reagent fluid is ejected from the manifold sample path through the corresponding nozzle member 48 onto substrate surface 26. As used herein, the term "non-contact" refers to the lack of contact between the dispense manifold and nozzles, and the target substrate during deposition. Typically, in these designs, the fluid is communicated through channels micromachined into an ink-jet style printhead—such as those commonly used in desktop and industrial printers.

Preferably, these ink-jet drop-on-demand dispensing actuators are coupled to digitally regulated hydraulic pressure systems (not shown). These systems enable precise manipulation of hydraulic pressure supplied to the dispensing actuators expanding the dynamic range of the system. An added benefit is the ability to quickly change the pressure range to compensate for differences in samples due to particulates or viscosity.

The aspiration source 21, on the other hand, are preferably provided by individual aspiration actuators 21 fluidly coupled to a corresponding first aspiration port 31 through tubing 61. These tubes 61, which are preferably inert plastic or the like having an inner diameter in the range of 0.2 mm to about 3.0 mm, are also separated into two banks of six units and each have a distal end coupled to a tubing array manifold 62. In turn, these opposed tubing array manifolds 62 are mounted to the stator manifold device 28 as a unit.

It will be appreciated that more than one or all of the aspiration conduits 30 can be fluidly coupled to a single aspiration actuator 21. In the preferred form, the aspiration actuator 21 is provided by an external metering device such as a syringe-type pump or a diaphragm pump, or by a pressurized source delivering a positive or negative pressure to the aspiration conduits 30. Typical of these aspiration devices is Model # 2009D provided by Innovadyne Technologies, Inc., Rohnert Park, Calif.

In another aspect of the present invention, the manifold device 28 is comprised of a plurality of stacked plate members 63-66 which collectively cooperate to channel the sample fluids from the reservoir wells to the designated test sites 25, via the valve assembly 27. As above-indicated, the manifold device 28 defines a plurality of primary passages 45, aspiration conduits 30 and dispensing conduits 35 each of which includes a communication port terminating at the stator face for communication with the valve assembly 27.

Since these individual conduits are independent of one another, fabrication is difficult for such a small scale. Typically, the diameter of these fluid passages is on the order of about 0.001 mm to about 1.0 mm. Moreover, these conduits and passages must be capable of accommodating the relatively high pressure pulses of the dispensing actuators 22 which as mentioned have a range from about $6.9(10)^3$ N/m$^2$ to about $138(10)^3$ N/m$^2$, and have a duration in the range from about $(10)^{-6}$ seconds to about $(10)^1$ seconds.

The plate members 63–66 (FIGS. 4 and 13) are preferably rectangular in shape, each having a substantially planar topside and an opposed bottom side. More particularly, the manifold device 28 includes a first plate member 63 having a topside surface 67 upon which the disk-shaped stator face element 53, defining the stator face 41, is supported. On an opposite side of the topside surface 67 of the first plate member 63 is a bottomside surface 68 upon which a plurality of horizontally extending dispensing grooves 70 are formed. These grooves are preferably about 0.3 mm in width and are about 1.0 mm deep into the bottomside surface 68, depending upon the particular application. A corresponding first dispensing port 36 extends vertically into the first plate member 63 from the topside surface 67 to the bottomside surface 68 where it intersects one end of a corresponding dispensing groove 70.

Similarly a corresponding second dispensing port 37 extends vertically into the stator face element 53 and first plate member 63 from the stator face 41 to the bottomside surface 68 where it intersects an opposite end of a corresponding dispensing groove 70.

In accordance with this aspect of the present invention, a substantially planar topside surface 71 of the second plate member 64 is affixedly lamination or diffusion bonded to the bottomside surface 68 of the first plate member 63 at a first plate/second plate interface. Hence, the diffusion bonded second plate member topside surface 71 effectively seals the dispensing grooves 70 extending into the bottomside surface 68 of the first plate member 63 to form the corresponding dispensing conduits 35.

It will be appreciated that the groove formation forming the horizontal portions of the dispensing conduits 35 could be provided by both the bottomside surface 68 of the first plate member 63 and the topside surface 71 of the second plate member 64, or alternatively, only by the second plate topside surface. It will further be understood that the alignment and orientation of first dispensing ports 36 can be positioned at a plurality of locations along the topside surface of the first plate member without departing from the true spirit and nature of the present invention.

Applying a similar technique, the aspiration conduits 30 could also have been defined at the first plate/second plate interface. However, to assure sufficient spacing between adjacent conduits to accommodate high pressure nature of the fluid delivery, the aspiration conduits 30 are preferably formed at a separate second plate/third plate interface between the second plate member 64 and a third plate member 65. Thus, the bottomside surface 72 of the second plate member preferably incorporates a plurality of horizontally extending aspiration grooves 73 (FIGS. 13 and 14) which are preferably about 0.5 mm in width and are about 0.25 mm deep.

A corresponding first aspiration port 31 extends vertically into the second plate member 64 from the topside surface 71 to the bottomside surface 72 thereof where it intersects one end of a corresponding aspiration grooves 73. It will be appreciated that the second plate member includes a pair of opposed wing portions 75 which extend beyond the peripheral edge of the first plate member 63. Briefly, these wing portions 75 are adapted to accommodate the mounting of the tubing array manifolds 62 thereto. Regarding the second dispensing ports 37, however, these aligned vertical passages extend from the stator face 41 of the stator face element 53 through both the first plate member 63 and the second plate member 64 to the bottomside surface 72 thereof where it intersects an opposite end of a corresponding aspiration groove 73.

Similar to the formation of the dispensing conduits 35, a substantially planar topside surface 76 of the third plate member 65 is affixedly coupled to the bottomside surface 72 of the second plate member 64 at the second plate/third plate interface. Again, applying conventional lamination or diffusion bonding techniques, the third plate topside surface 76 can be laminated to the second plate bottomside surface 72 to effectively seal the aspiration grooves 73 to form the corresponding aspiration conduits 30.

Figure 4B:
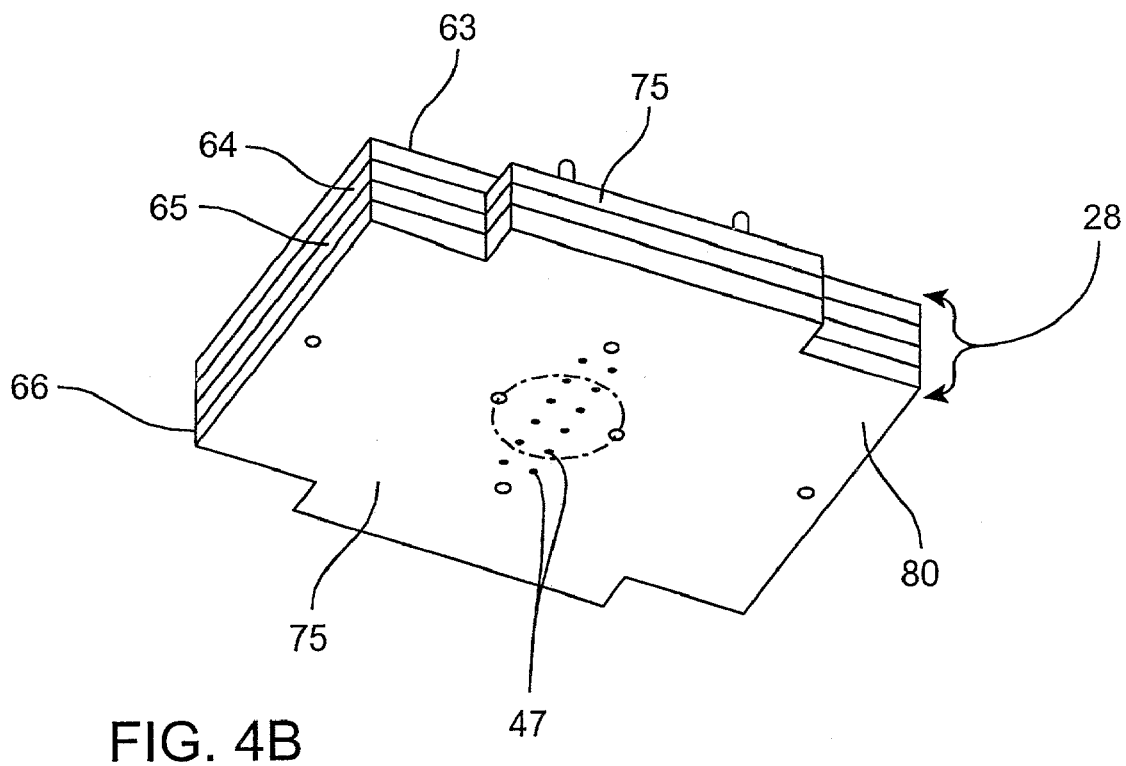
FIG. 4B is a bottom perspective view illustrating the lower communication ports of the manifold device of FIG. 4A.
Figure 4A:
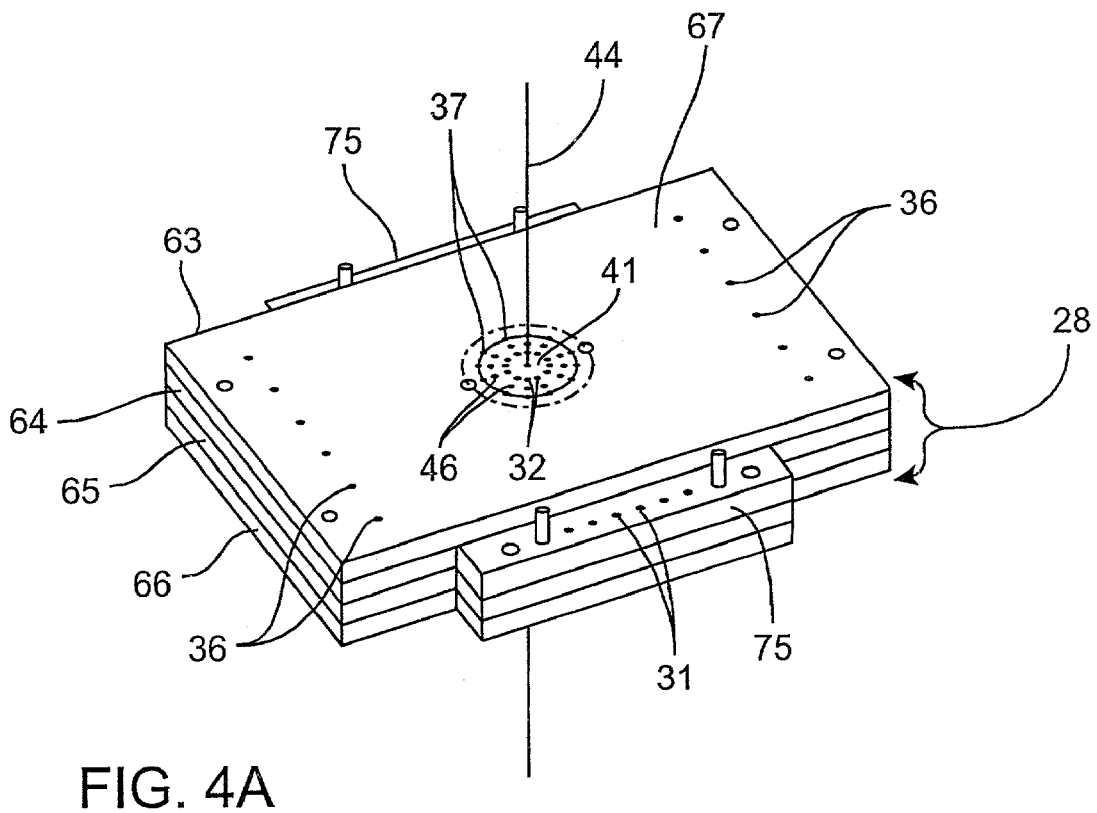
FIG. 4A is a top perspective view of a manifold device of the hybrid valve apparatus of FIG. 1, and illustrating the stator face interface.
Figure 13:
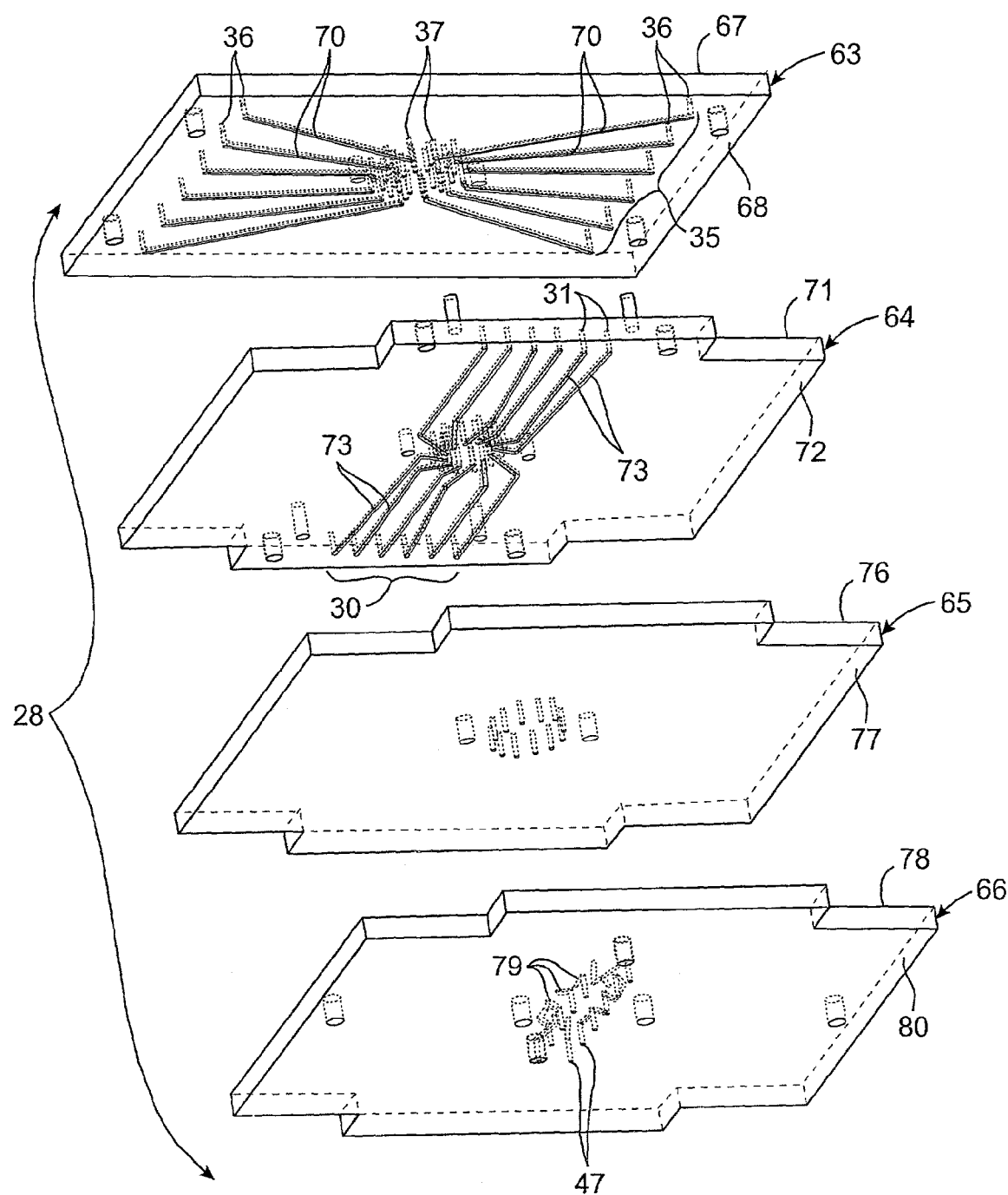
FIG. 13 is an exploded, enlarged bottom plan view of the manifold device of FIG. 4B, illustrating the channels and grooves of the individual plate members.
Figure 14:
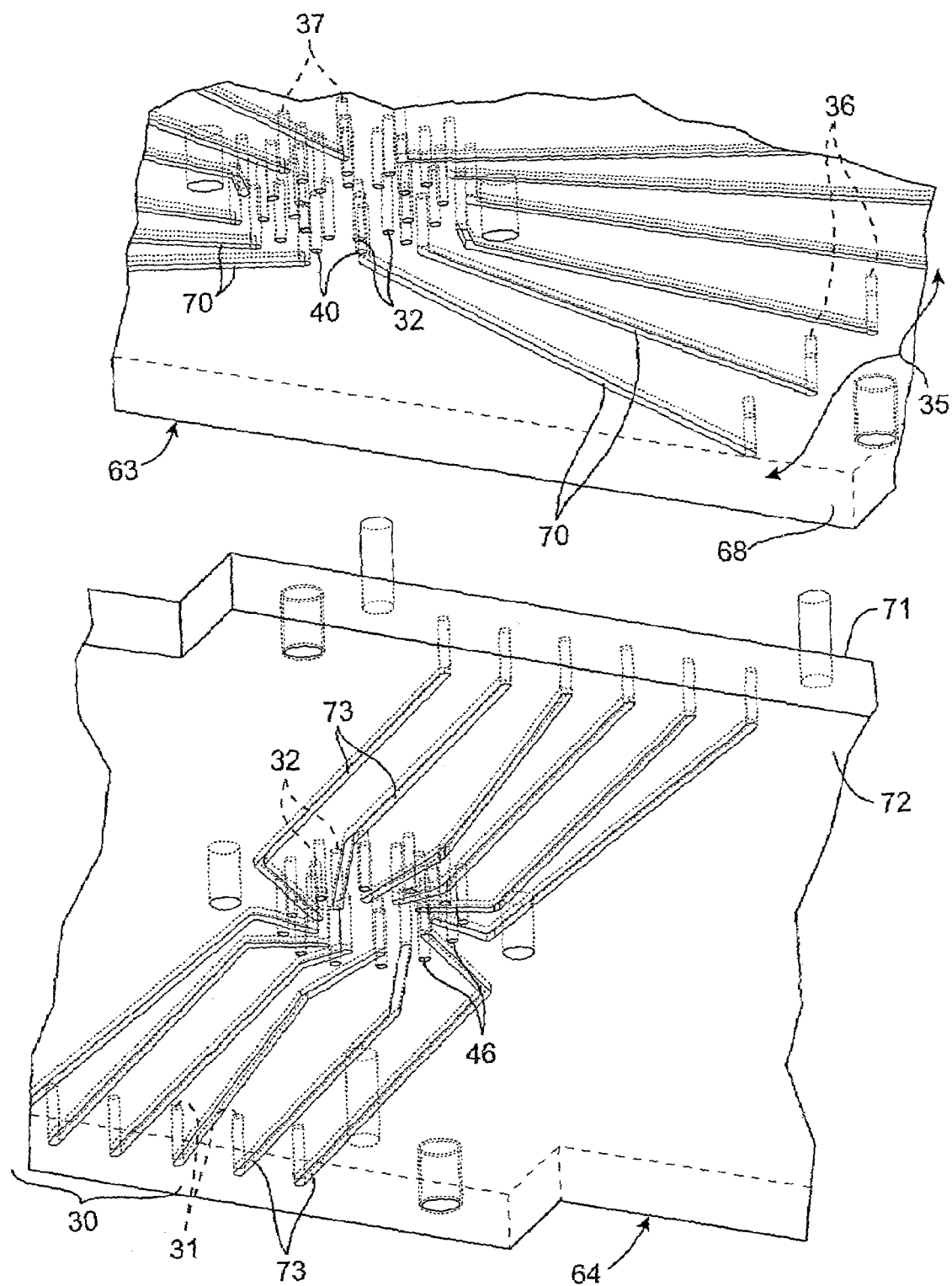
FIG. 14 is an enlarged, fragmentary, illustration of the exploded bottom plan view of FIG. 13.

As best viewed in FIGS. 4A and 13, the circular pattern of the upper communication port 46 extend vertically through the stator element 53. The first plate member 63, the second plate member 64 and the third plate member 65 also include corresponding co-axially aligned passage components to collectively form the primary passages 45 of the sample paths 33 when the manifold plate members are laminated together. Typically, the transverse cross-sectional area of primary passages 45 are on the order of about 0.2 mm$^2$ to about 0.8 mm$^2$ from the stator face 41 to a bottomside surface 77 of the third plate member 65.

To reorient the circular pattern of the upper communication port 46 at the bottomside surface 77 of the third plate member 65 to a rectangular pattern of the lower communications ports 47, which conforms to the spacing of the array of reservoir wells 38 of the microtiter plate 40 and test sites 25, a fourth plate member 66 is required. As shown in FIGS. 10, 12 and 13, a fourth topside surface 76 of the fourth plate includes a plurality of horizontally extending repositioning grooves 79. These grooves 79 are preferably about 0.5 mm in width and are about 0.25 mm deep into the topside surface 76 of the fourth plate member 66. A corresponding lower communication port 47 extends vertically into the fourth plate member 66 from a bottomside surface 80 to the topside surface 78 thereof where it intersects one end of a corresponding repositioning groove 79. The other end of the repositioning groove 79 is aligned with the corresponding primary passage 45 terminating at the bottomside surface 77 of the third plate member 65. Again, applying conventional lamination or diffusion bonding techniques, the fourth plate topside surface 78 can be diffusion bonded to the third plate bottomside surface 77 to effectively seal the repositioning grooves 79 to form another portion of the sample path 33.

As above-mentioned and as illustrated in FIGS. 2, 5 and 6, fluidly coupled to each lower communication port 47 of the primary passage 45 is a corresponding nozzle member 48 having a nozzle passage 50 extending therethrough. The elongated nozzle member 48 includes a distal tip portion 81 suitably dimensioned to extend into a targeted reservoir well 38, in aspiration condition, to aspirate sample or reagent fluid into the sample path 33. Moreover, the 2×6 array of nozzles are spaced apart to conform with the array of reservoir wells and test sites 25 for simultaneous aspiration and dispensing. They can also be redistributed to other formats such as 1×12.

In the preferred embodiment, the diameter of the nozzle 50 passages abruptly changes to a smaller diameter by means of an orifice, such as a jeweled orifice. This change in diameter is beneficial in that it facilitates ejection of the sample fluids from the tip when a pressure pulse is delivered by the corresponding dispensing actuator 22.

As shown in FIG. 3, system fluid reservoirs 82, 83, containing conventional mobile phase fluid 85, 86, are supplied to the aspiration actuators 21 and the dispensing actuators 22 as a driving fluid. In the aspiration condition, when rotor element 52 of the valve assembly 27 is rotated to align the corresponding aspiration channels 57 to the corresponding upper communication ports 46 of the primary passages 45 of the sample paths 33 and the second dispensing ports 37 of the aspiration conduits 30, the aspiration actuators 21 can be first employed to purge the entire path from the first aspiration port 31 of the aspiration conduit all the way to the corresponding dispensing orifice of the tip 81 of the nozzle member 48. Thus, after the nozzle tips are optionally cleaned, clean mobile phase fluid replaces any sample or reagent fluid from previous operations.

The transport mechanism (not shown) is then operated to position the hybrid valve assembly 27 at the reservoir wells 38 where the designated nozzle tips 81 are submersed in the targeted reservoir wells. Operation of one or more of the syringe pumps 21 draw the sample or reagent fluids into the corresponding sample path 33 in the manifold device 28. The volume of fluid aspirated into the corresponding sample path 33, thus, can be accurately metered.

Subsequently, the transport mechanism can move the hybrid valve assembly 27 to the test sites 25, while the electric motor 56 and drive train 54 rotates the rotor element 52 from the aspiration condition to the dispensing condition. As mentioned, the aspiration channels 57 in the rotor face 51 are moved out of fluid coupling to the upper communication ports 46 of the primary passages 45, while the dispensing channels 58 in the rotor face 51 are moved to fluidly couple the second dispensing ports 37 of the dispensing conduits 35 with the corresponding communication ports 46. Essentially, in the aspiration condition, the second dispensing port 37 of the dispensing conduit 35 is dead-ended against the rotor face 51, while in the dispensing position, the second aspiration port 32 of the aspiration conduit 30 is dead-ended against the rotor face 51.

The mobile phase fluid, which is preferably substantially similar to that supplied to the aspiration actuators, is fluidly coupled to the corresponding dispensing channels 58 in the rotor face 51 to selectively dispense the sample fluids from the corresponding nozzle tips 81. Accordingly, cross-contamination is minimized to the mobile phase fluids contained in the corresponding dispensing channels 58. This assures that the dispensing conduits 35 can be substantially maintained free of contamination of any sample or reagent fluids.

In an alternative embodiment of the present invention, the nozzle passages 50 and corresponding primary passages 45 may only be employed to dispense the sample or reagent fluid from the sample path 33. Unlike the embodiment above-mentioned, the nozzle member 48, thus, will not be utilized to aspirate the targeted fluid into the sample path from the source plate. Accordingly, as viewed in the embodiments of FIGS. 15 and 17, the hybrid valve assembly can load the sample path 33 through means other than the nozzle members 48, while maintaining the isolation of the sample path from the dispensing actuator, in the aspiration condition (FIGS. 15 and 17), and isolation of the sample path from the aspiration actuator, in the dispensing condition (FIGS. 16 and 18).

Briefly, the manifold body in this configuration includes a source conduit, generally designated 87, having an upper communication opening 88 terminating at the stator face 41, and an opposite end in fluid communication with the source reservoir 23. Further, as best viewed in FIGS. 15, 17 and 19, the contact or rotor face 51 of the valve body or rotor element 52 includes a sample channel 90 which, in the aspiration condition, fluidly couples the second aspiration port 32 of the aspiration conduit 30 to the upper communication opening 88 of the source conduit 87.

Figure 17:
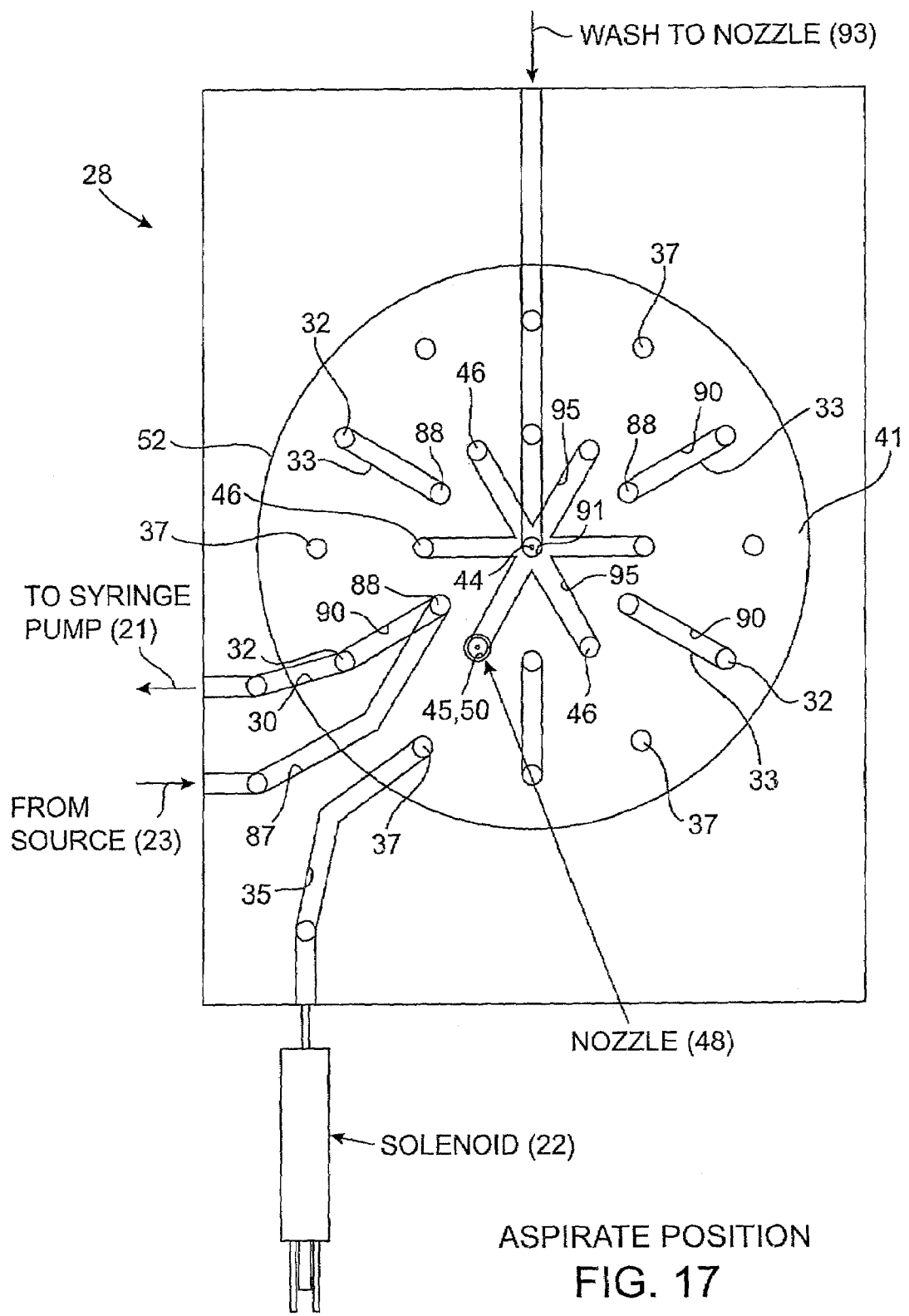
FIG. 17 is an enlarged top plan view of the rotor/stator interface of FIG. 15, in the aspiration condition.

Accordingly, in the aspiration condition, the aspiration actuator 21 is fluidly coupled to the source reservoir through the sample channel 90 formed in the rotor face 51. Upon activation of the aspiration actuator, the reagent or sample fluid can be drawn into the sample path 33 by way of the source conduit 87 in the manifold body 28. To isolate the dispensing actuator 22 from the sample path 33, the corresponding second dispensing port 37 of the dispensing conduit 35 is dead-ended into the rotor face 51, and thereby out of fluid communication with the sample path (FIG. 17).

Figure 16:
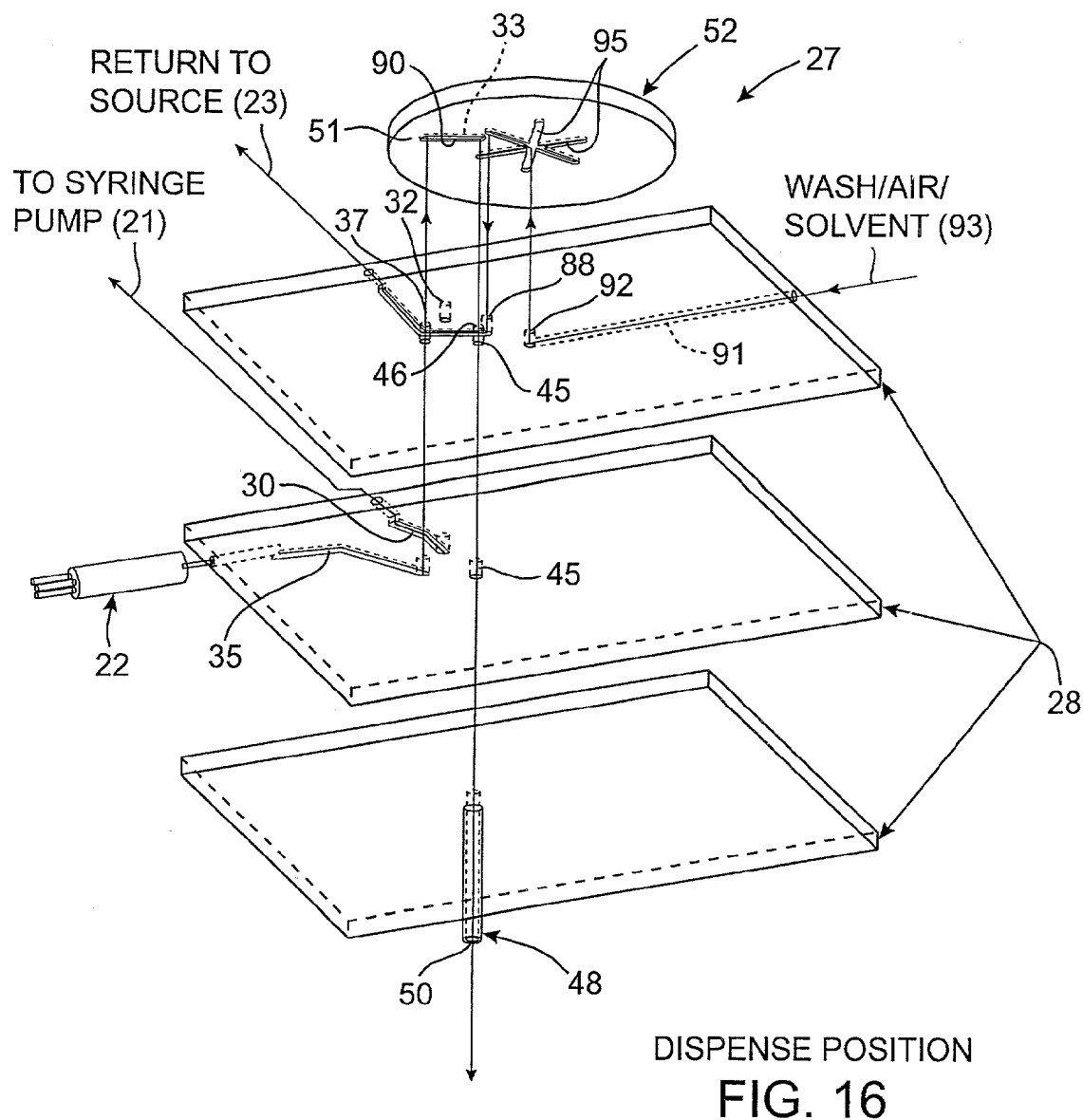
FIG. 16 is an exploded bottom perspective view of one fluid path of the alternative embodiment hybrid valve apparatus of FIG. 15, in the dispensing condition.
Figure 18:
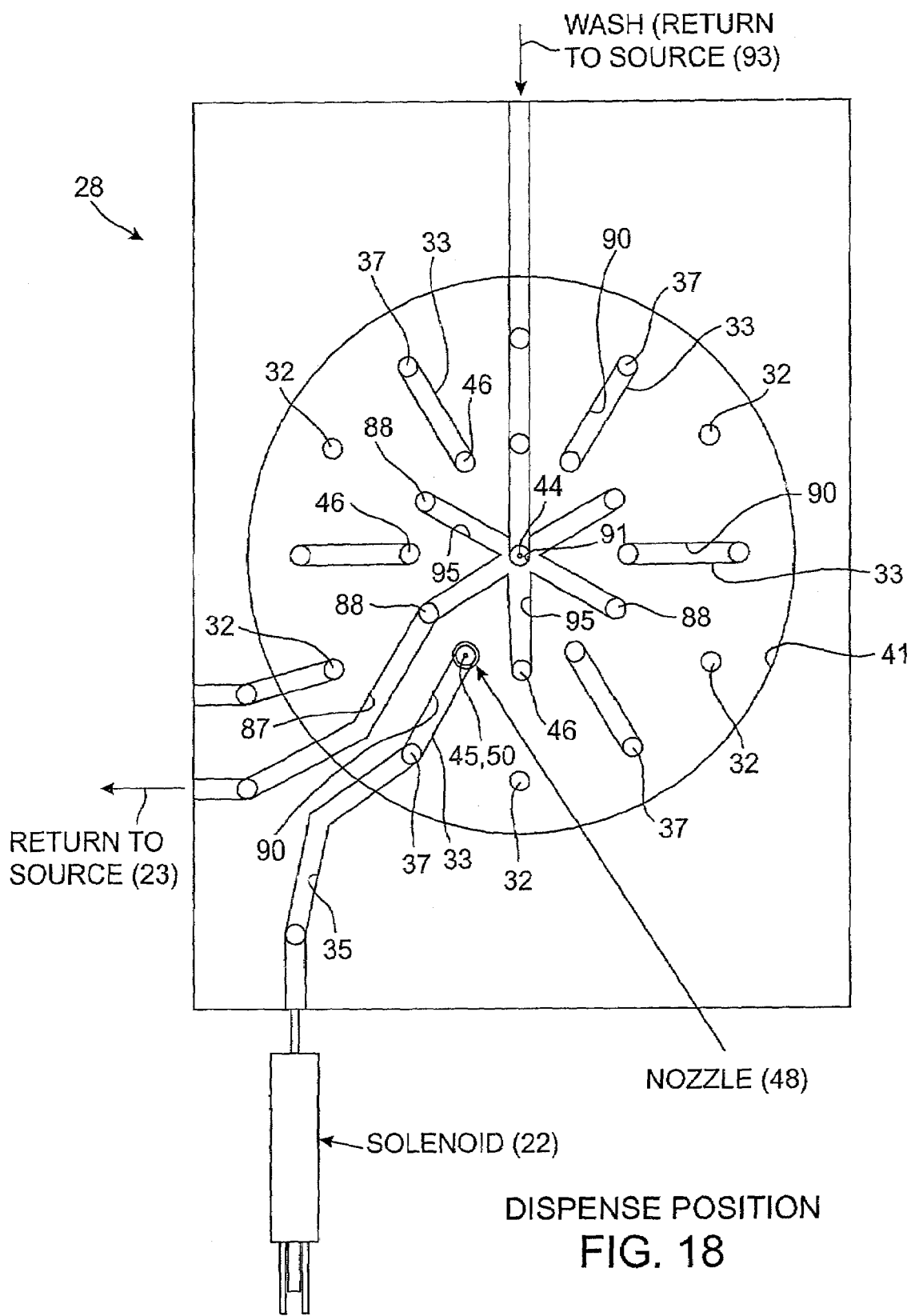
FIG. 18 is an enlarged top plan view of the rotor/stator interface of FIG. 16, in the dispensing condition.

Once the reagent or sample fluid is aspirated into the sample path 33, via the aspiration actuator 21, the valve assembly 27 can be moved to the dispense position of FIGS. 16 and 18. In the preferred form, the rotor element 52 of the valve assembly is rotated about rotational axis 44 for movement from the aspiration condition to the dispense condition. The sample channel 90, containing the reagent or sample fluid, is co-aligned with and moved into the fluid communication with the second dispensing port 37 of the dispensing conduit 35 and the upper communication port 46 of the primary passage 45. The dispensing actuator 22 is therefore fluidly coupled to the sample path 33 to fluidly dispense the reagent or sample fluid out of the nozzle member 48. Moreover, to isolate the aspiration actuator 21 from the sample path 33, the corresponding aspiration port 32 of the aspiration conduit 30 is dead-ended into the rotor face 51, and thereby out of fluid communication with the sample path (FIG. 18).

In this embodiment, thus, it will be appreciated that the dispensable volume of the sample path 33 is essentially the same as that of the sample channel 90. When the rotor element 52 rotates to the dispensing condition (FIGS. 16 and 18), only the sample or reagent fluid contained in the sample channel 90 is fluidly accessible to the dispensing actuator. It will be understood, however, that volumetric quantities less than the full volume of the sample channel 90 may be dispensed through precision operation of the dispensing actuator 22.

Figure 19:
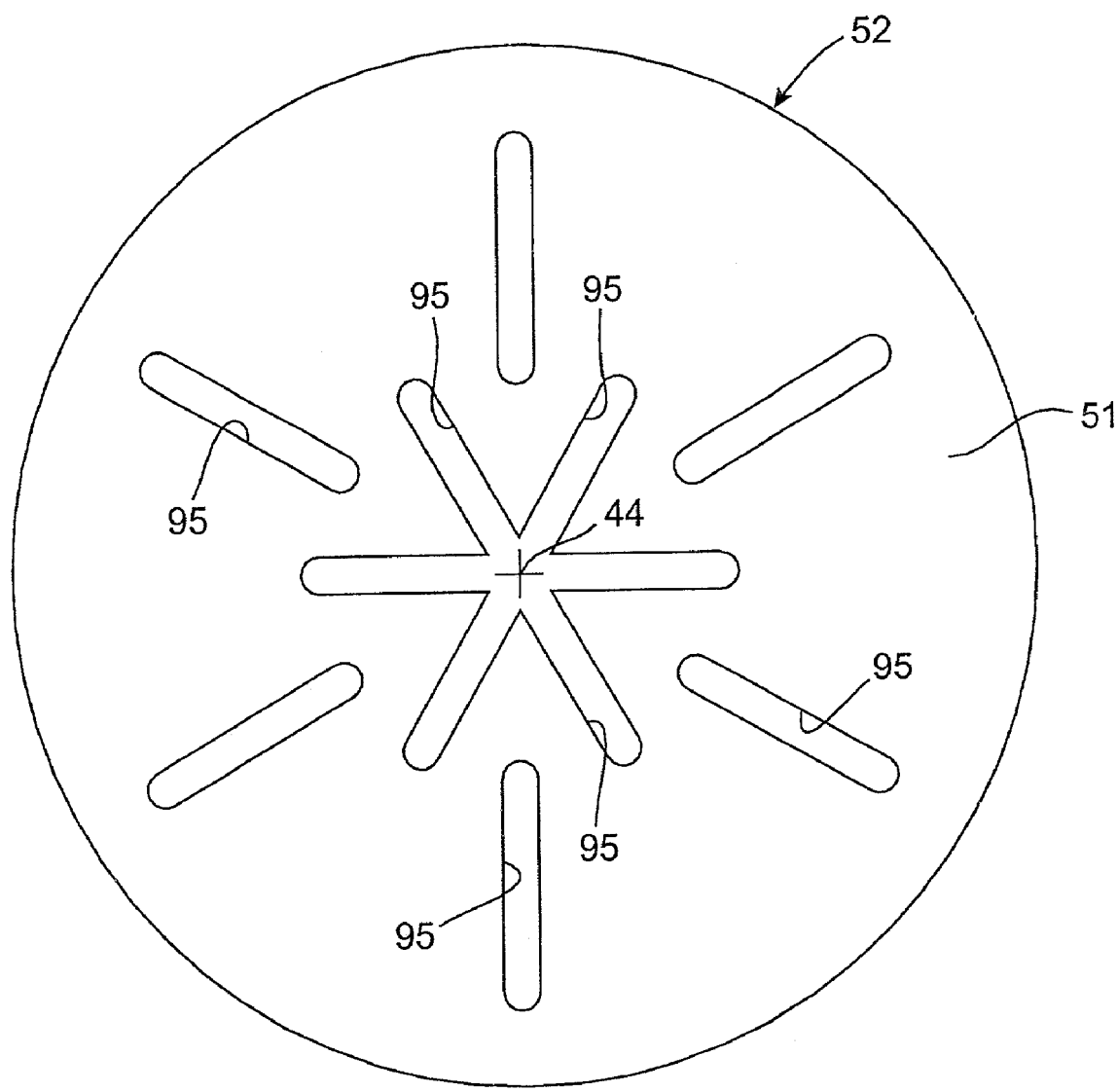
FIG. 19 is an enlarged, bottom plan view of the rotor face of the alternative embodiment rotor element

As best shown in FIG. 19, each sample channel 90 is slotted into the substantially planar rotor face 51 of the rotor element 52. Further, each equally spaced sample channel 90 is elongated in shape, and extends generally along a radial line intersecting the rotational axis 44 of the rotor face 51. Accordingly, at the rotor-stator interface (i.e., the high pressure sliding contact between the stator face 41 and the rotor face 51), the rotor element 52 either reciprocates or rotates in one direction clockwise or counter clockwise to orient the valve assembly in the aspiration condition or the dispensing condition.

These sample channels 90 preferably have a length in the range of about 1.0 mm to about 6.0 mm, and have a transverse cross-sectional area of about 0.3 $mm^2$ to about 1 $mm^2$. Accordingly, the volumetric capacity of the sample channel 90 is preferably in the range of about 0.5 µl to about 2.0 µl. In comparison, the primary passage 45 and the nozzle passage 50 of the outlet preferably has a volume in the range of 0.1 µl to about 2.0 µl.

The separation of the aspiration duty from the nozzle member 48 has several functional advantages. One benefit is that the total volume of sample is contained in the sample channel 90. Unused sample or reagent may be returned to the source, during dispense (FIG. 18) via the source path 23 significantly reducing sample and reagent waste volumes. An added benefit is that the nozzle member 48 may be greatly reduced in length to shorten the dispense path and pre-dispensing.

Another benefit of this design is that a spacing and order of the source reservoir array does not need to match that of the targeted test sites. That is, since the nozzle member 48 are not employed for both the aspiration and dispensing functions, the aspiration inlets (not shown), fluidly coupled to source conduits 87, can be set at one spacing and order (e.g., 96 well format), while the nozzle members 48 can be set to a different spacing and order (e.g., 1536 well format). Accordingly, the aspiration versatility is substantially increased. For example, some applications require individual manipulation of aspiration tips, such as applications that reformat individual positive samples to one destination plate from a multiplicity of positive and negative samples in a source plate.

In yet another advantage of this design, the transverse cross-sectional dimension of the aspiration and source conduits 30, 87, on the aspiration side, can be different from that of the dispensing conduits 35 and the primary passages 45 in the manifold device 28 and the nozzle passages 50 of the nozzle member 48, on the dispensing side. For example, it would be desirable to provide a large bore aspiration conduit 30 and source conduit 87 to facilitate rapid sample aspiration into the sample channel. In contrast, it would be desirable to provide a smaller bore for the nozzle passages 50 to facilitate ejection of smaller discrete volumes. Otherwise, when a smaller bore is utilized for restrictive flow of the dispense nozzle, in the previous embodiment, effective aspiration is compromised.

Lastly, the permissible wider cross-sectional dimension of the aspiration inlet allows for the inclusion of filtering devices. For example, by incorporating a filter on the inlet side, small particulates in the reagent or sample fluid that would normally clog, and render useless, a small bore nozzle can be removed. Such a filter could be exchangeable and would contain a high surface area allowing for filtering of particulates without frequent clogging. Typical of such filtering devices include frits commonly used in solid phase extraction or liquid chromatography devices.

Referring back to FIGS. 15 and 16, this embodiment of the present invention may further include a flush passage 91 in the manifold device 28 having an upper central flush port 92 terminating at the stator face 41, and an opposite end in fluid communication with a flush source 93. The central flush port 92 is aligned substantially co-axial with the rotational axis 44 of the rotor element 52 for continuous fluid communication with a flush channel 95 slotted in the rotor face 51 (FIG. 19).

Figure 15:
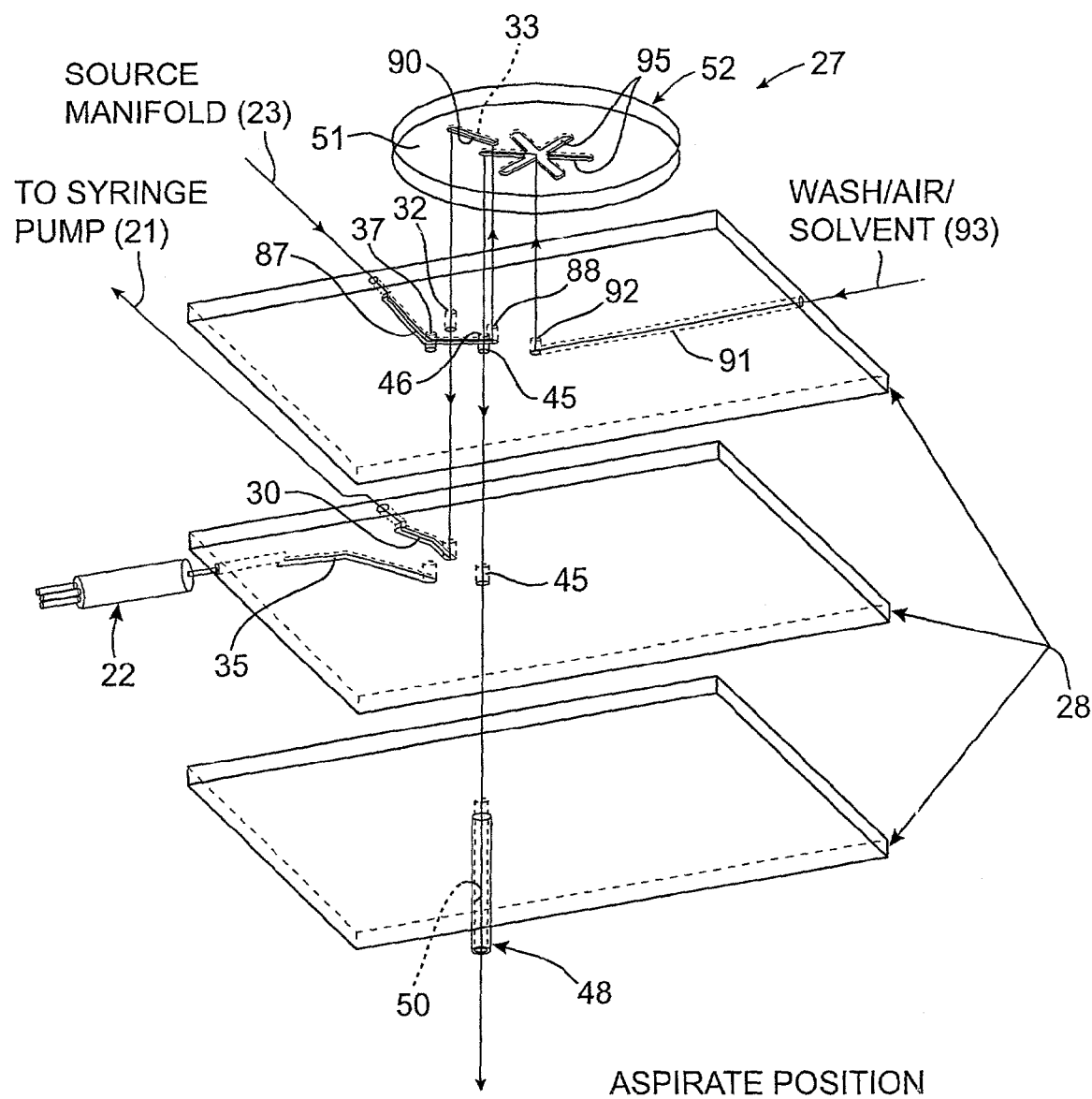
FIG. 15 is an exploded bottom perspective view of one fluid path of an alternative embodiment hybrid valve apparatus in the aspiration condition.

In the aspiration condition of FIGS. 15 and 17, this flush channel 95 in the rotor element 52 is fluidly couples the flush port 92 of the flush passage 91 to the upper communication port 46 of the corresponding primary passage 45. Thus, while the reagent or sample fluid is being aspirated into the corresponding sample path 33, the primary passages 45 and the nozzle passages 50 may be simultaneously flushed or cleaned with wash fluid or the like from the wash source 93. In contrast, when the rotor element is rotated to the dispensing condition of FIGS. 16 and 18, the flush channel 95 slotted in the rotor face fluidly couples the flush port 92 of the flush passage 91 to the upper communication opening 88 of the source conduit 87. Therefore, when the reagent or sample fluid is being dispensed from the sample path 33 through the corresponding nozzle member 48, unused sample or reagent could be returned to the source reservoir 23 and the aspirate path flushed.

Figure 20:
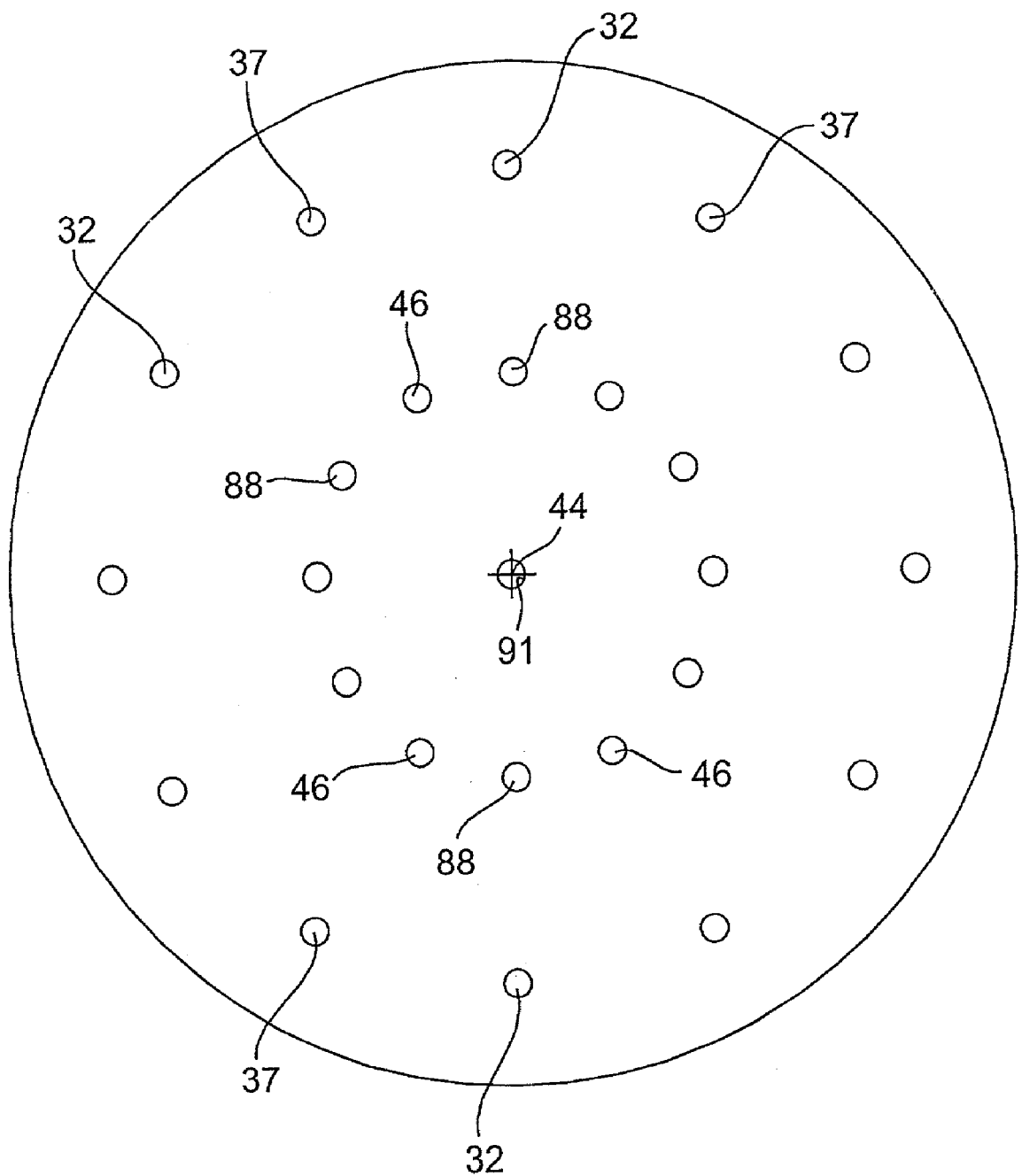
FIG. 20 is an enlarged, top plan view of the stator face of the stator element of the alternative embodiment rotor element.

Preferably, the flush channel 95 is provided by a plurality of equally spaced elongated slots which extend generally along a radial line intersecting the rotational axis 44 of the rotor face 51. These radially extending flush channels intersect at the rotational axis 44 so that the flush channels are in continuous fluid communication with the central flush port 92. As shown in FIG. 20, the upper communication ports 46 of the primary passages 45 and the upper communication openings 88 of the source conduits 87 are alternately spaced about the rotational axis 44. Accordingly, each rotation movement of the rotor element 52 between the aspiration condition (FIGS. 15 and 17) and the dispensing condition (FIGS. 16 and 18) alternates fluid communication with the nozzle passages 50 and the source conduits 87.

Accordingly, at the rotor-stator interface (i.e., the high pressure sliding contact between the stator face 41 and the rotor face 51), the rotor element 52 either reciprocates or rotates in one direction clockwise or counter clockwise to orient the valve assembly in the aspiration condition or the dispensing condition.

Figure 21:
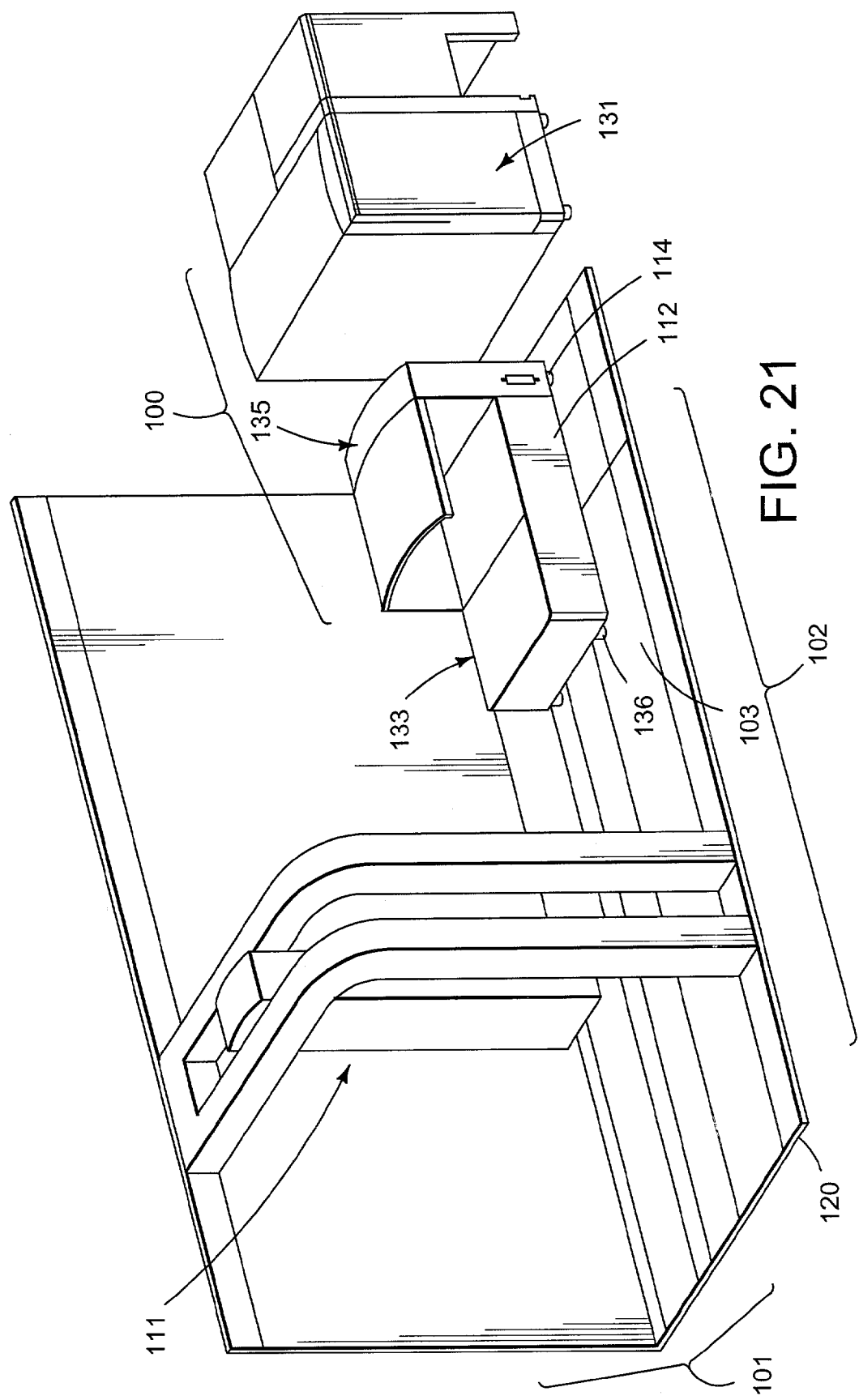
FIG. 21 is a top perspective view of an automated fluid handling system with a secondary fluid dispensing system constructed in accordance with the present invention.

In another aspect of the present invention, as viewed in FIGS. 21–24, a removable secondary liquid dispensing module or peripheral, generally designated 100, is provided for use with an existing, automated liquid handling system 101 (FIG. 23) adapted to provide or enable the performance of one or more microbiological procedures. The automated liquid handling system 101 defines a work area 102 having a plurality of discrete work stations 103. Each of the work stations 103 provides a lab ware site 105 and alignment structure 106 enabling aligned receipt and removal of the sample carriers 107 at respective lab ware site 105. Each sample carrier 107, which is preferably provided by standardized microtiter or microwell plates 107, provides a plurality of test or sample sites 108 therein for sample analysis of a sample or other type of molecular biology procedures. The automated liquid handling system 101 further includes a plate positioning mechanism 110 (FIG. 23) and a primary liquid dispensing device 111 (FIG. 21). The plate positioning mechanism is configured to move and position the microtiter plates 107 to and from the lab ware sites 105 of the respective work stations 103 thereof and into engagement with the respective carrier alignment structure 106 thereof. The primary liquid dispensing device 111 is configured for selective contact-type dispensing of discrete quantities of fluid, in the range of about one (1) microliter to about ten (10) milliliters, into the test sites 108 of the microtiter plates 107 secured in the respective alignment structure of the respective work station 103.

In accordance with the present invention, the removable secondary liquid dispensing peripheral 100 includes a chassis or base member 112 dimensioned to be positioned or fit substantially within a footprint of one or more of the discrete work stations 103, and mounting hardware 113 adapted to removably secure the base member 112 in the work station 103. A support platform 115 is affixed to the base member 112, and is configured to support a micro titer-plate 107. An alignment mechanism 116 is configured to removably align and position a plate-plate 107 therein by the robotic plate positioning mechanism 110 of the automated liquid handling system 101. The support platform 115 and alignment mechanism 116 cooperate to form and provide a peripheral lab ware site 117 suitable for secured receipt of a plate-plate 107 therein. The secondary liquid dispensing peripheral 100 further includes a secondary liquid dispensing device, generally designated 118, which is operationally independent from the primary liquid dispensing device 111. The secondary dispensing device 118 is further adapted for selective non-contact-type dispensing of discrete quantities of fluid, in the range of about one (1) nanoliter to about ten (10) microliters, into the test sites 108 of the plate-plate 107 positioned in the peripheral lab ware site 117.

Accordingly, the removable and secondary liquid dispensing peripheral 100 of the present invention may be removably mounted to and within the footprint of one or more of the work stations 103 of an existing conventional liquid handling system that cannot accurately accommodate sub-microliter fluid dispensing. The addition of the self-contained secondary liquid dispensing peripheral 100, thus, enables a more precise fluid delivery of a sample or reagent fluids, at sub-microliter volumes, into the sample carrier test sites that the automated fluid handling system upon which it resides is incapable of. Thus, the versatility and liquid delivery range of these current liquid handling systems can be significantly and accurately improved at the sub-microliter volumes. This would then enable these existing automated liquid handling systems to perform the sub-microliter microbiological procedures above-mentioned, while at the same time maintain capability for increased liquid dispension through the primary liquid dispensing device. However, when it is desirable to dispense smaller discrete quantities of fluid, in the range of about one (1) nanoliter to about ten (10) microliters, which these existing primary liquid dispensing systems are not designed, the more refined and accurate secondary liquid handling system of the present invention may be utilized.

Figure 23:
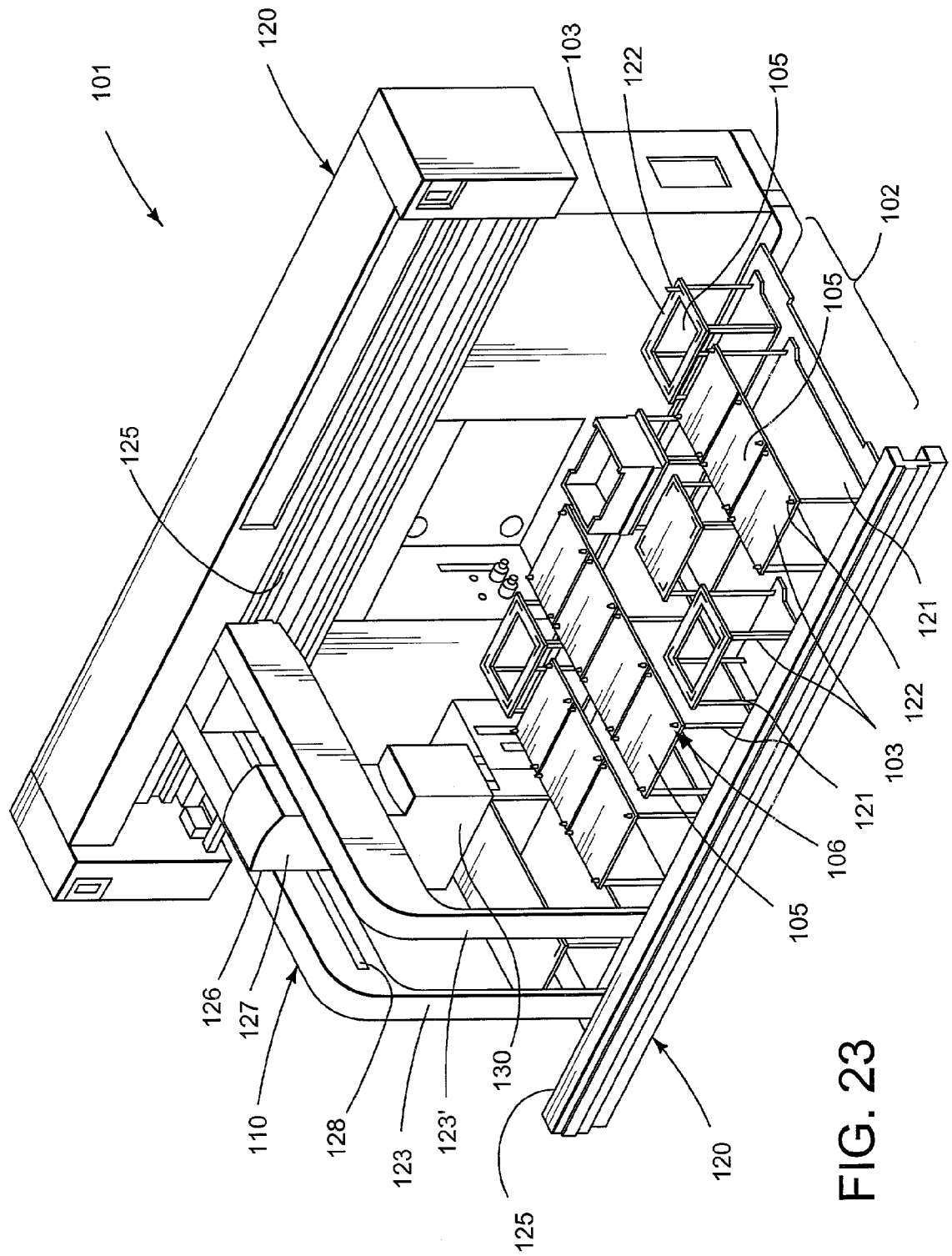
FIG. 23 is a reduced top perspective view of one specific embodiment of the automated fluid handling system of FIG. 21.
Figure 24:
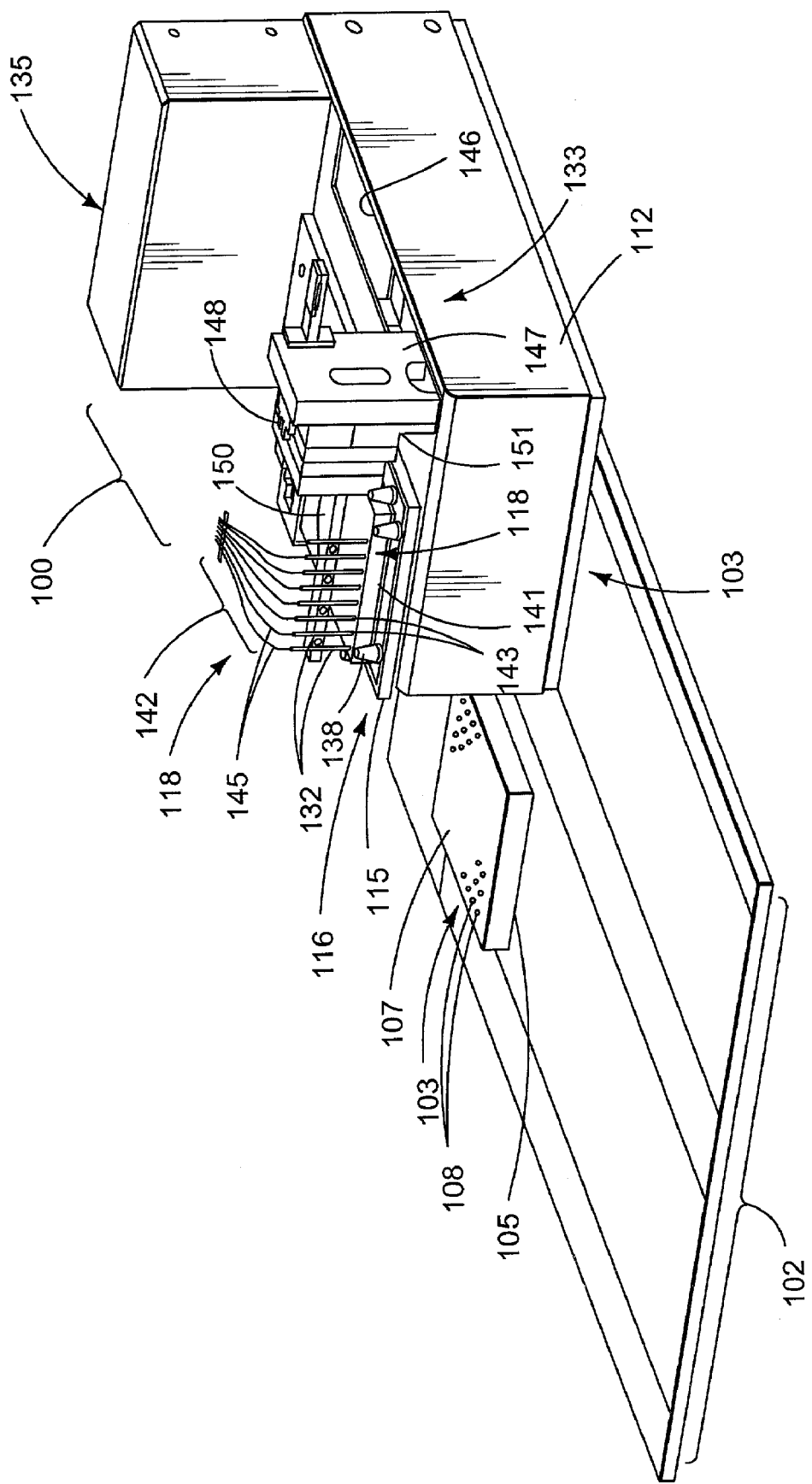
FIG. 24 is an enlarged top perspective view of the secondary liquid dispensing system mounted to one of the work stations of the automated fluid handling system, both of FIG. 21.

Referring now to FIGS. 21 and 23, and in accordance with the present invention, the automated liquid handling system 101 is shown having a frame assembly 120 positioned about the work area 102. The work area 102 preferably provides a plurality of work stations, each including a lab ware site 105, aligned in an array. These lab ware sites 105 are aligned and positioned a discrete locations or positions within the work area so that precision liquid handling procedures can be performed on the sample contained in the test sites 108 of the sample carriers 107. Such procedures, by way of example, may include High Throughput Screening (HTS).

Briefly, these sample carriers 107 include a plurality of test sites 108 aligned in an array so that more than one sample may be processed at any given time. These microtiter or microwell plates (used interchangeably herein) are generally applied in these sample analysis protocols, and are typically provided by plastic plates defining uniformly spaced depressions or wells (i.e., test sites 108) that contain the fluid dispensing therein. These commercially available rectangular plates typically include eight rows of twelve microwells that provide an industry-standard ninety-six microwell plate, such as plate 40 shown in FIG. 3. Other conventional sizes include sixteen rows of twenty-four microwells that provide three hundred eighty-four microwells.

Moreover, the present invention is capable of extending the dispense resolution of these automated liquid handling systems to sixteen rows of twenty-four microwells that provide 1536 microwells, which these systems cannot normally handle. In particular, the positioning devices of many of the automated liquid handling systems are not capable of moving to all the positions on a 1536-well plate. In these instances, the automated liquid handling system can be fitted with a sample transfer device like a "gridding head" (a head with 1536 pins that transfers sample by surface tension) and then apply the secondary liquid handling peripheral to add reagents. That is, the secondary liquid handling peripheral generally provides a positional resolution that that is much better than the primary liquid handler. Another advantage of this is that if multiple, robotically-interfaced, primary systems are used, and one of them is 1536 capable, the labware (plates) processed on that instrument could be transferred to the system with our device and further processing could occur.

In accordance with the present invention, the lab ware sites 105 preferably conform to a uniform screening standard to simplify operation, versatility and uniformity in conformance to other screening procedures. In particular, one or more of the lab ware sites conform to a Society of Bimolecular Screening (SBS) standard micro titer-plate lab ware site which is commonly applied in HTS. Thus, the alignment structure 106 of each lab ware site 105, that enables removal and securing of the microtiter plates 107 thereof, also conforms to that of the Society of Bimolecular Screening standard micro titer-plate lab ware site.

As best viewed in FIG. 23, one or more of the work stations 103 enclosed in the work area 102 includes a support base 121 to support a lab ware object (e.g., a microtiter plate 107 or a lab ware peripheral 100). To secure or align a lab ware object in the respective lab ware site 105 of the work station, the alignment structure 106 is provided to cooperate with the support base 121. By way of example, for an SBS standard micro titer-plate lab ware site attachment, the alignment structure may include a plurality of strategically placed conical-shaped locators 122 that contact and engage the a microtiter plate 107 (not shown) placed therein to align and position the plate in the respective lab ware site 105. These conical-shaped locators 122 are preferably composed of a substantially rigid, metallic material such as stainless steel Thus, when the positioning mechanism 110 vertically lowers the gripped microtiter plate 107, as will be described below, the strategically placed conical-shaped locators 122 position and align plate in the lab ware site 105. In other alignment arrangement, the conical-shaped locators may be movable or inwardly biased for increased securement and alignment of the plate.

It will be appreciated that while only a microtiter plate 107 has been described as removably engaging the alignment structure 106 at each lab ware site, other lab ware or peripheral structures may be removably mounted thereto. By way of example, this may include mixers, shakers, incubators, centrifuges, test tube racks, and large reagent reservoirs, as well as the secondary liquid handling system of the present invention, as will be described in greater detail below.

The automated liquid handling system 101 of FIGS. 21 and 23 further includes a universal positioning mechanism 110 movably mounted to the frame assembly 120 thereof. The positioning mechanism 110 is configured to move and position the lab ware objects to and from the respective lab ware sites 105 and into or out of engagement with the respective carrier alignment structure 106 of the respective work stations 103. In particular, these preferably robotic positioning mechanisms 110 employ a three-axis X-Y-Z Cartesian system to accurately move and position the lab ware object (i.e., microtiter plates 107) to the discrete positions of the lab ware sites so that a lab procedure can be performed.

In one specific configuration, the positioning mechanism 110 includes a pair of spaced-apart, inverted, L-shaped robotic arms 123, 123' that are movably mounted to the frame assembly 120 through a rail system 125 or the like for tandem movement along an X-axis direction thereof (FIG. 23). For example, the rail system may include a lead screw coupled to a stepper motor, or a linear actuator (both of which are not shown) for selective automated or manual displacement of the robotic arms 123, 123' along the X-axis. Other conventional techniques can of course be employed as well.

FIG. 23 further illustrates that the positioning mechanism 110 includes a positioning head device 126 disposed between the spaced robotic arms 123, 123' for displacement along the Y-axis direction. The positioning head device 126 includes base portion 127 which is movably coupled the spaced-apart L-shaped robotic arms 123, 123' through a track system 128. This arrangement enables selective linear displacement of the positioning head along the Y-axis direction for alignment with the work stations.

Finally, the positioning head device 126 includes a gripping head 130 adapted to grip and manipulate the lab ware objects for placement and positioning into and out of the lab ware sites 105 of the work stations. The gripping head 130 includes conventional gripping structure to grip and manipulate lab ware objects such as a microtiter plate 107.

This gripping head 130 is moveably mounted to the support base 121 for selective displacement thereof along the Z-axis (FIG. 23). This mechanical movement, for instance, may provide telescopic, rotational or linear motion control mechanism. This movement enables gripped lab ware objects to be vertically displaced toward or away from the respective alignment structure 106 of any one of the plurality of the Society of Bimolecular Screening (SBS) standard micro titer-plate lab ware site.

Accordingly, the collective cooperation of the X, Y and Z displacement components of the positioning mechanism 110 enable accurate placement and positioning of the gripped microtiter plate 107 anywhere within the work area. Moreover, while the controlled movement of each component of the positioning mechanism 110 has been described with respect to conventional rail and track systems, stepper motors and other conventional mechanical positioning apparatus, it will be appreciated that other variations would include, but are not limited to linear motion controls systems, servo controlled systems, and pneumatic motion control systems.

To provide the primary liquid delivery of these automated liquid handling system, a primary liquid dispensing device 111 is incorporated (FIG. 21). As mentioned, these existing fluid delivery devices typically provide fluid delivery through contact-type fluid delivery nozzles (not shown) in volumes greater than about one (1) microliter. These nozzles are generally aligned in an array with spacings similar to that of the test sites of a micro titer plate, and are carried by a positioning device with movement similar to the X, Y and Z displacement components of the positioning mechanism 110 (i.e., the gripping head 130, positioning head 126 and L-shaped robotic arms 123, 123'). This enables the contact-type fluid delivery nozzles to be positioned for contact-type fluid delivery directly in the selected wells of the microtiter-plates.

Moreover, typical of such lab work stations that provide such microliter to milliliter fluid dispensing performance include, for example, the Hamilton MicroLab 4200 liquid handling device by the Hamilton Company of Reno, Nev., the BIOMEK® FX Liquid Handling Workstation, the BIOMEK® 2000 Workstation, both from Beckman Coulter, Inc. of Fullerton, Calif., illustrated in FIG. 23. Briefly, as shown and mentioned above, these automated liquid handling systems include the frame assembly 120, the positioning mechanism 110 and primary liquid dispensing device 111 for handling, positioning and liquid dispensing of and into microtiter plates 107. A plurality of work stations 103 are aligned in an array enclosed within the work area, and are accessible by the positioning mechanism 110 and primary liquid dispensing device. In this embodiment, each work station 103 is and the corresponding alignment mechanism 116 conform to the universal method of attachment of a Society of Bimolecular Screening standard micro titer-plate lab ware site.

In accordance with the present invention, a secondary liquid dispensing peripheral or module 100 is provided for installation in the work area of the automated liquid handling system 101 which can operably function simultaneously with the primary liquid dispensing device 111. This secondary liquid dispensing peripheral 100 is mountable to one or more of the work stations 103 (FIG. 23), and provides accurate, non-contact fluid delivery in the range of about one (1) nanoliter to about ten (10) microliters. Thus, together with the contact-type liquid dispensing capabilities of the primary liquid dispensing device 111, which as mentioned delivers fluids in the range of about one (1) microliter to about ten (10) milliliters, the versatility and the capabilities of the automated liquid handling system are significantly increased. By enabling accurate fluid delivery in the sub-microliter range of fluid dispensing, precision liquid dispensing can be provided for microbiological laboratory procedures and analysis once not inherently possible with these existing liquid handling systems.

The secondary liquid dispensing peripheral 100 itself includes a standardized lab ware site 105 thereon that permits receipt of a sample carrier 107 therein. More particularly, the peripheral lab ware site conforms to the Society of Bimolecular Screening standard for micro titer-plate lab ware sites so that these standardized microtiter plates can be positioned, removed, aligned and secured therein directly from the positioning mechanism 110 of the automated liquid handling system. Moreover, the secondary liquid dispensing peripheral 100 is a self-contained fluid dispensing unit that is operationally independent from the primary liquid handling unit. Accordingly, when secondary liquid handling system is mounted to one of the work stations 103 within the work area 102, both the primary liquid handling device and the secondary liquid handling device can operate simultaneously and independently without interference from one another.

The secondary liquid handling peripheral 100 will now be described in detail. Referring now to FIGS. 21, 22, 25 and 26, the self-contained secondary liquid dispensing peripheral 100 is shown including a fluid control component 131 (FIG. 25) that controls the non-contact fluid delivery through a plurality of dispense nozzles 132, a motion control component 133 (FIG. 26) that selectively positions the nozzles 132, as a unit, to dispense the reagent or sample fluids into the test sites 108 of the peripheral positioned micro titer plate 107, and an operation interface component 135 (FIG. 26) for stand-alone or remote control operation of the two components.

Figure 26:
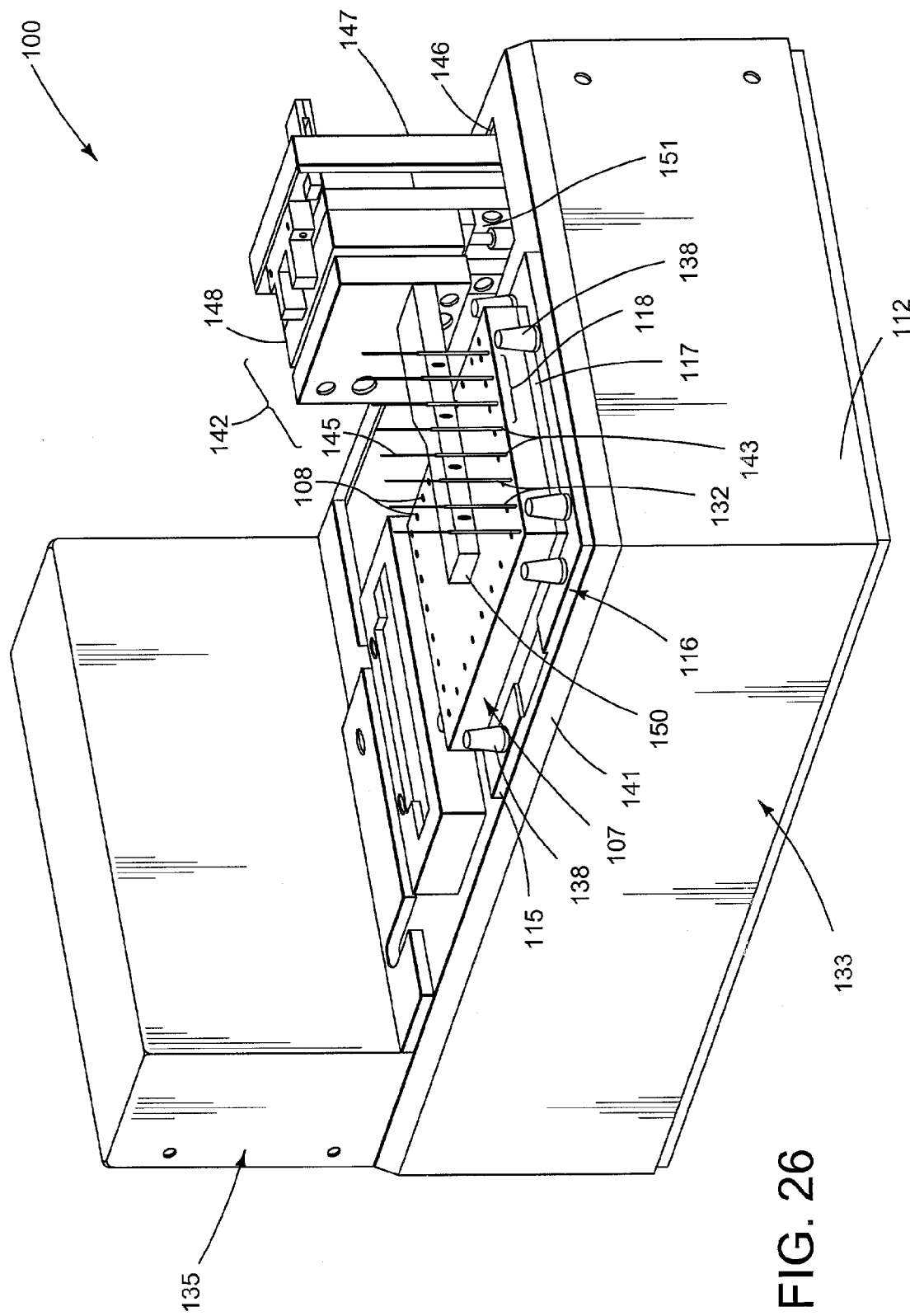
FIG. 26 is an enlarged top perspective view of a motion control module of the secondary liquid dispensing system of FIG. 21.
Figure 27:
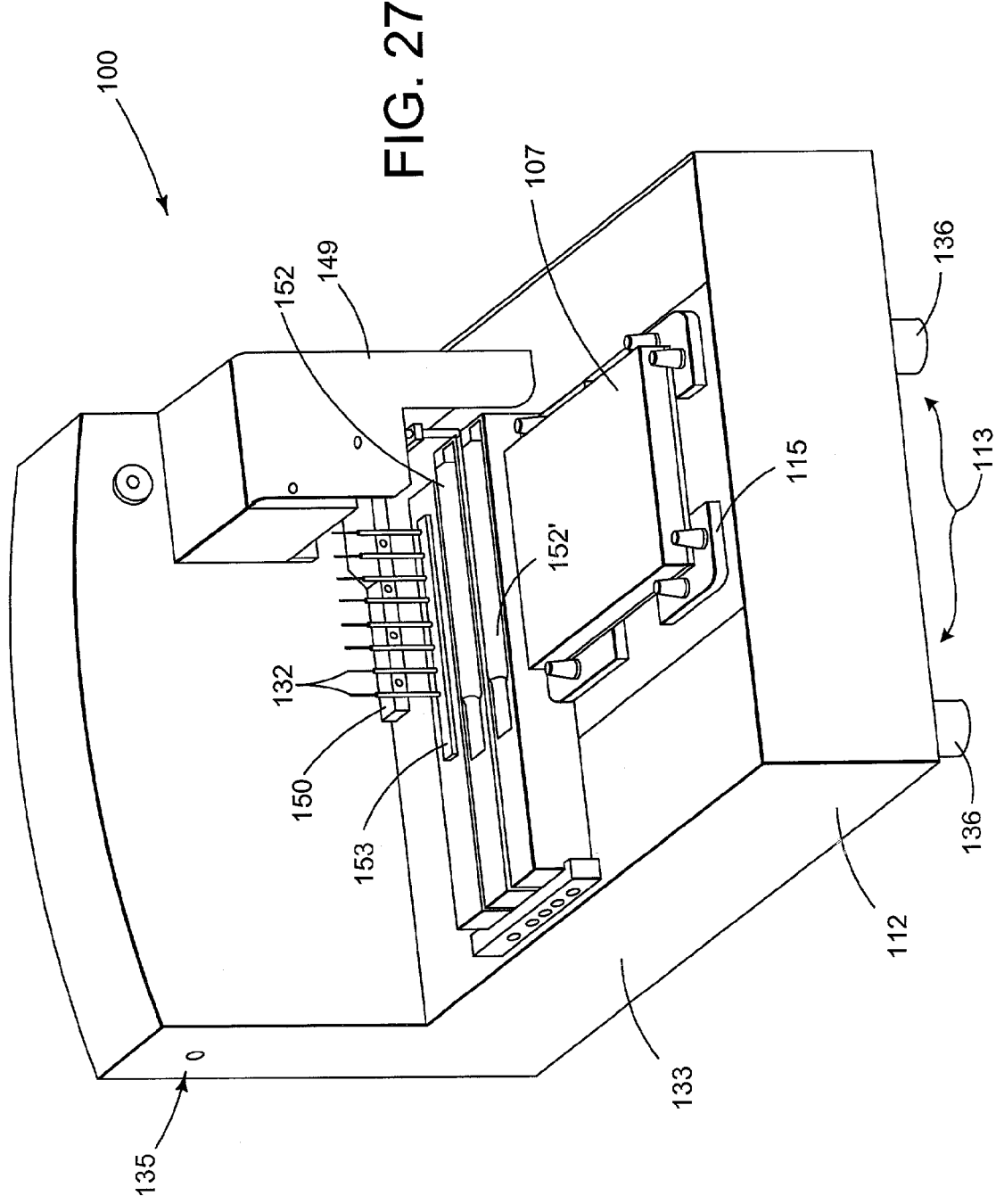
FIG. 27 is another top perspective view of the motion control module.
Figure 28:
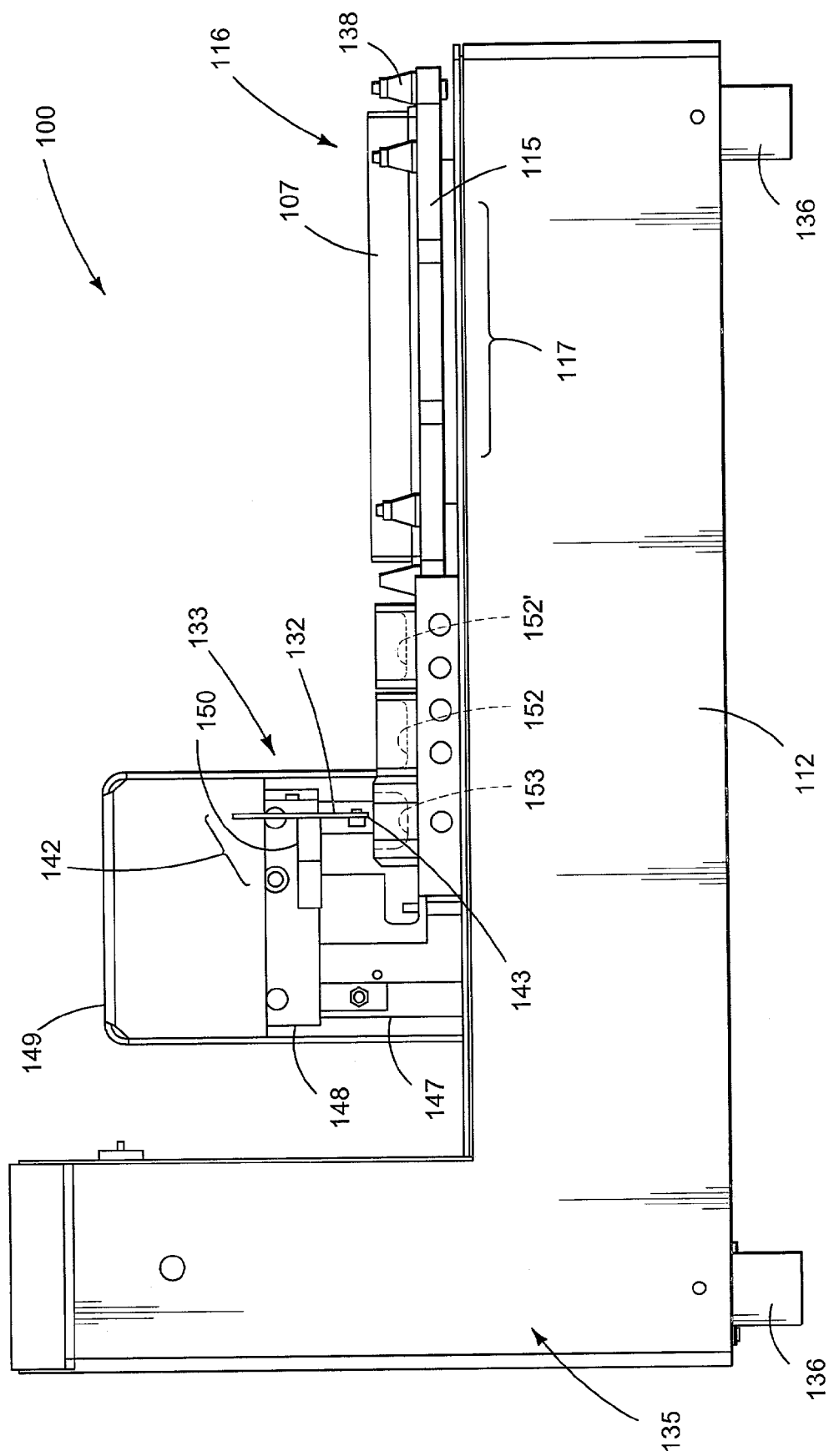
FIG. 28 is an enlarged, side elevation view of the motion control module of FIG. 21 with the dispense head in a "Wash Home" position.

The motion control component 133, as best viewed in FIGS. 26–28, includes a base member 112 which is removably mountable to the lab ware site 105 of the respective work station 103. As above indicated, in particular, the base member 112 includes mounting hardware 113 (FIG. 27) that is adapted to attach to an SBS standard micro titer-plate lab ware site. In one configuration, for example as shown in FIGS. 21 and 28, the mounting hardware 113 is provided by spaced-apart mounting posts 136 situated at the bottom corners of the base member 112. These posts 136 are aligned and slidingly received in correspond slots 114 of the respective work station alignment structure 106 (in conformance with the SBS standard) to removably secure the secondary liquid dispensing peripheral 100 to that lab ware site.

In accordance with the present invention, the base member 112 itself defines an SBS standard micro titer-plate lab ware site 117 situated atop the support platform 115. This standardized peripheral lab ware site 117 and the support platform 115 are strategically positioned such that when the mounting hardware 113 of the base member 112 engages the associated alignment structure 106 of the respective work station 103, the peripheral lab ware site 117 atop the support platform 115 is accessible by the positioning mechanism 110 of the automated liquid handling system 101. This enables cooperation between the positioning mechanism 110 and the secondary liquid dispensing peripheral to position and remove a sample carrier 107 in and from the peripheral lab ware site 117.

In another embodiment, the base member may be simply situated atop the support platform of the work station 103 in a manner positioning the alignment structure 116 near the coordinates of the respective work station lab ware site 105. The robotic positioning mechanism is then employed to determine the precise location of the microtiter plate positioned in the peripheral lab ware site 117.

As best illustrated in FIGS. 26–29, the SBS standardized alignment structure 116 of the secondary liquid dispensing peripheral 100 includes a plurality of upstanding conical locators 138 that strategically surround a sample carrier receiving area 140 (FIG. 29) of the peripheral lab ware site 117. In the specific embodiment illustrated, at least two spaced-apart conical locators 138 are provided for each of the four sidewalls 141 of the conventional rectangular SBS standard micro titer plate 107.

Thus, to load a micro titer-plate 107 in the receiving area 140 of the peripheral lab ware site 117, the positioning mechanism 110 of the automated liquid handling system 101, similar to the delivery technique employed for the conventional SBS standard micro titer-plate lab ware site attachment, will position the gripped plate 107 vertically above the receiving area 140. As the gripping head 130 of the positioning mechanism lowers the gripped micro titer plate 107 into the receiving area 140 of the peripheral lab ware site 117, the sidewall 141 of the micro titer plate 107 contact and engage the locators 138. The conical shape of these substantially rigid locators 138 function to urge the micro titer plate 107 into alignment in the receiving area. In other alignment arrangements, it will be understood, the conical-shaped locators may be movable or inwardly biased for increased securement and alignment of the plate.

Turning now to FIGS. 26–28, the motion control component 133 is illustrated including a fluid dispense head 142 carrying the plurality of non-contact dispense nozzles 132 for selective positioning above the mounted microtiter-plate to dispense discrete sub-microliter quantities of fluid into the targeted test sites 108. Briefly, these spaced-apart dispense nozzles 132, similar to those above-mentioned that are directly mounted to the hybrid valve apparatus 20, include distal dispense ends 143 that are adapted for precision volume, non-contact liquid dispensing, and opposite ends fluidly coupled to flexible tubing 145 (FIG. 22) sufficient to enable movement of the nozzles about the micro titer plate 107. In turn, the opposed ends of the flexible tubing 145 are fluidly coupled to the fluid control component 131 which will be discussed in greater in detail below.

To move the dispense head 142 for selective precision positioning of the array of dispense nozzles 132 vertically above the targeted test sites 108 of the micro titer plate 107, the motion control component 133 preferably employs a conventional three-axis X-Y-Z Cartesian system. Applying a precision track or rail system 146, for example, a control post 147 is movably mounted to the base member 112 for incremental displacement along the Y-axis (FIG. 26). The dispense head 142 is then movably mounted to the control post 147 through an arm portion 148 which can be vertically displaced along the Z-axis, while further capable of being extended or retracted along the X-axis. A shield or cover 149 is positioned around the control post 147 for protection (FIGS. 27 and 28). The arm portion 148 of the dispensing head 142 includes a support bracket 150 vertically supporting the plurality of dispense nozzles 132 above the microtiter plate 107. In one specific arrangement, the dispensing head provides eight (8) dispensing nozzles aligned in a linear array having dispensing ends 143 equally spaced-apart by a distance conforming to the spacing of the wells or test sites 108 of the microtiter plate 107.

The precision track or rail system 146 for the X-axis displacement preferably includes a lead screw and precision stepper motor arrangement between the control post 147 and the base member 112. In contrast, the precision track or rail system 151 (FIG. 26) for the Y-axis and Z-axis precision displacement are preferably provided by conventional linear actuators. It will be appreciated, of course, that any of the X, Y or Z-axes displacements may be provided by any conventional linear displacement techniques, including but not limited to linear motion controls systems, servo controlled systems, and pneumatic motion control systems. Alternatively, the motion control may move the SBS standard lab ware site 117 to a position where the non-contact dispensing is performed.

Accordingly, a multi-channel dispense head 142 is provided that is essentially mounted on a three axis X-Y-Z Cartesian "pick and place" motion platform. Through the precision track or rail devices, stepping motors or the like, and through the three-axis motion control component 133, motion control of the dispense head can be independently performed along the X, Y, and Z axis. By way of example, the Z-axis displacement positions the dispense ends 143 of the dispense nozzles closer or further from the test sites 108 of the micro titer plate 107 for such non-contact fluid dispensing. Similarly, the X-axis and Y-axis displacement of the dispense head enables any one of the dispense nozzles to be aligned with any one of the test sites in any row or column of the micro titer plate 107.

Figure 29:
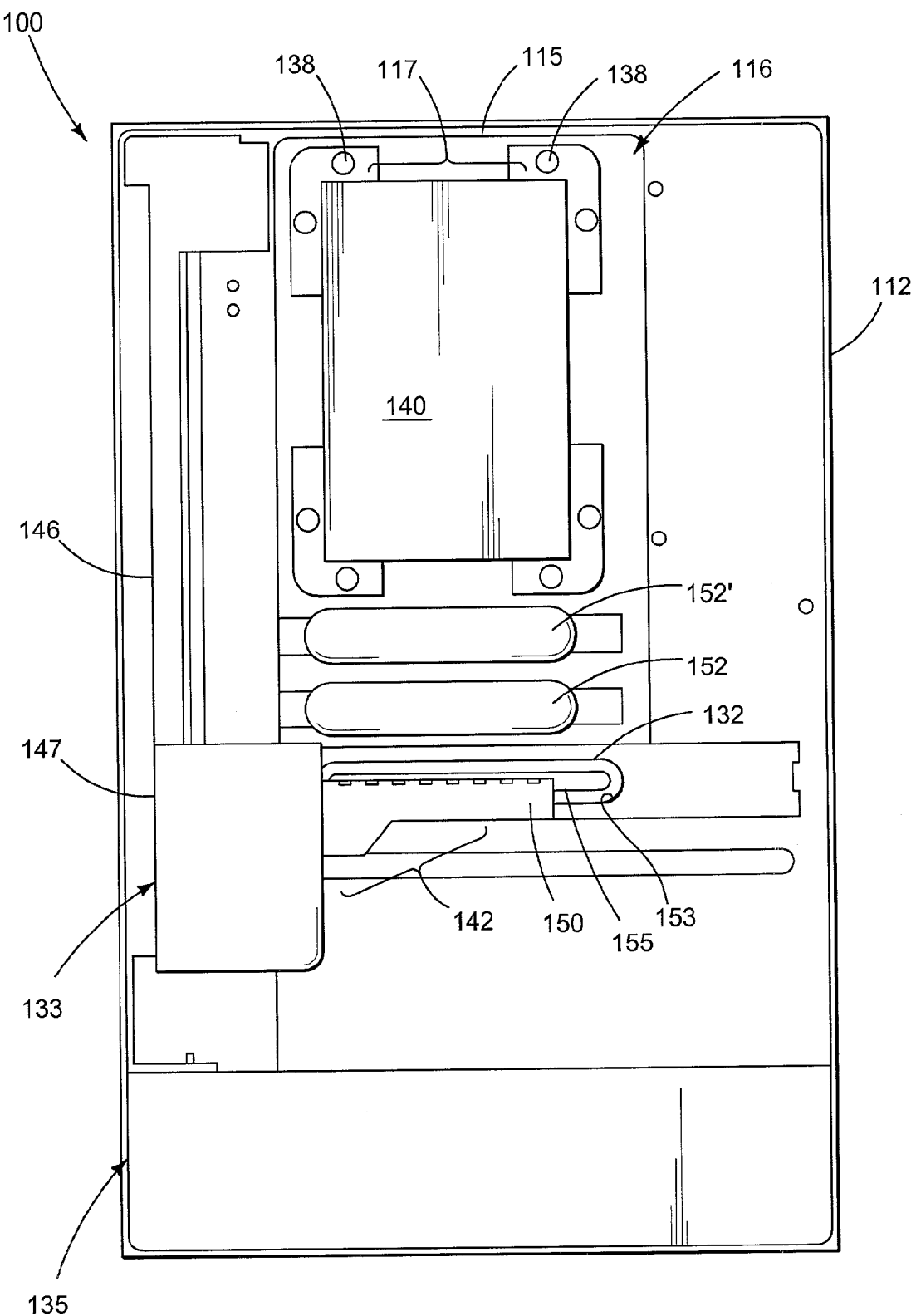
FIG. 29 is a top plan view of the motion control module of FIG. 28.

Referring now to FIGS. 27–29, a pair of reagent containers 152 and 152' are provided atop the support platform 115, adjacent the peripheral lab ware site 117. These reagent containers 152, 152' are elongated wells adapted to contain reagent fluid therein to provide a fluid reservoir of sample or reagent during an aspiration procedure or condition, as described above, and as will be described in accordance with the description of the fluid control component below. As best viewed in FIGS. 27 and 29, the elongated reagent wells 152, 152' are formed in manner enabling simultaneous immersion of the dispensing ends 143 (tips) of the dispense nozzles in the wells during aspiration into the fluid control component. Providing two adjacent reagent containers enables the use of two different reagents for simultaneous immersion. Alternatively, each container can be compartmentalized in various configurations to enable multiple reagent reservoirs (not shown).

The motion control component 133 further includes a wash station 153, adjacent the reagent container 152, to wash and rinse the dispense ends 143 of the dispense nozzles, and/or discard excess reagent or sample fluids contained in the nozzles and flexible tubing. Similar to the reagent containers 152, 152', the wash station 153 is provided by an elongated well adapted to contain wash fluid therein, and dimensioned to enable simultaneous immersion of the dispensing ends 143 (tips) of the dispense nozzles in the wash fluid. During a wash or fluid discard procedure, when the dispense head is moved to the "parked" or "wash home" positioned shown in FIGS. 27–29, the reagent or sample fluid contained in the tubing and nozzles is flushed into the well of the wash station 153. As the nozzle tips are immersed in the wash fluids in the wells, and the reagent fluids are purged from the nozzles, the flow past the tips functions to wash the outside of the tips. The wash station 153 includes a drain port 155 at the bottom of the well for draining the wash, rinse or discarded fluid.

Figure 22:
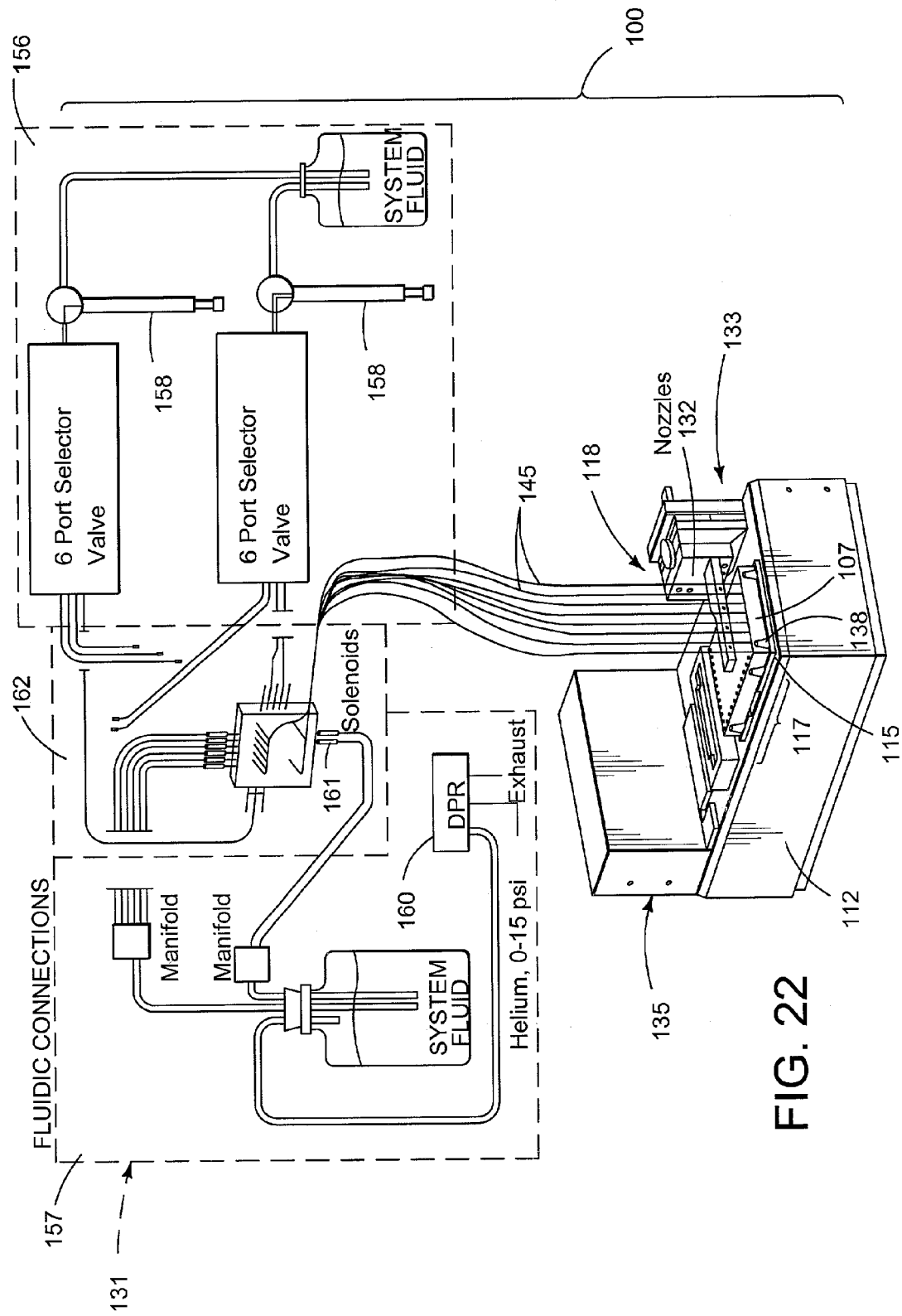
FIG. 22 is a schematic diagram of the secondary liquid dispensing system of FIG. 21.

Referring now to the fluid control component 131 (FIGS. 22 and 25), all fluid aspiration into the system and all sub-microliter fluid dispension from the non-contact dispense nozzles 132 is controlled. FIG. 22 illustrates that the fluid control component 131, briefly, contains a fluid aspiration (input) subsystem 156, a fluid dispensing (output) subsystem 157, a fluid switching subsystem 162 fluidly coupled therebetween, dispense valving 161, fittings and flexible tubing 145 fluidly coupled to the dispense nozzles 132. Collectively, this arrangement delivers precision quantities of sub-microliter fluids from the non-contact dispense nozzles in the range of about one (1) nanoliter to about ten (10) microliters.

Generally, the fluid control component 131 of the present invention includes two types of fluid metering components: a pressure system and a switching valve. The first metering component meters input of fluid into the system (into the dispense ends 143 of the dispense nozzles), while the second type of metering controls fluid output or dispense from the dispense nozzles. The input subsystem or fluid aspiration subsystem is generally a macro volume system aspirating fluid volumes greater than one (1) microliter of fluid into the dispensing ends 143 of the dispense nozzles when positioned in contact with the source fluid, such as when the dispensing ends are immersed in the reagent fluid contained in the reagent container. It will of course be appreciated that sample fluids can be aspirated as well. The dispensing subsystem 157, on the other hand, is designed to dispense fluid volumes less than one (1) microliter (i.e., sub-microliter volumes) of fluid out of the dispensing ends 143 of the dispense nozzles out of contact with the destination substrate.

In one specific configuration, the fluid aspiration (input) subsystem 156 is provided by one or more syringe drives 158, while the fluid dispensing (output) subsystem 157 is provided by a pressure subsystem 160 and one or more ink jet solenoid valves 161. To fluidly couple the fluid aspiration subsystem 156 and the fluid dispensing subsystem 157 through the dispense nozzles, the respective fluid channels for each subsystem are connected through the fluid switching subsystem 162 that switches between an aspiration condition and a dispensing condition. Preferably, the fluid switching subsystem 162 is provided by the multiple path, hybrid valve apparatus 20 and switching valve assembly 27 which includes the rotatory shear face valve/hybrid manifold combination discussed above to effect precision switching between the fluid aspiration system and the fluid dispensing system.

Figure 25:
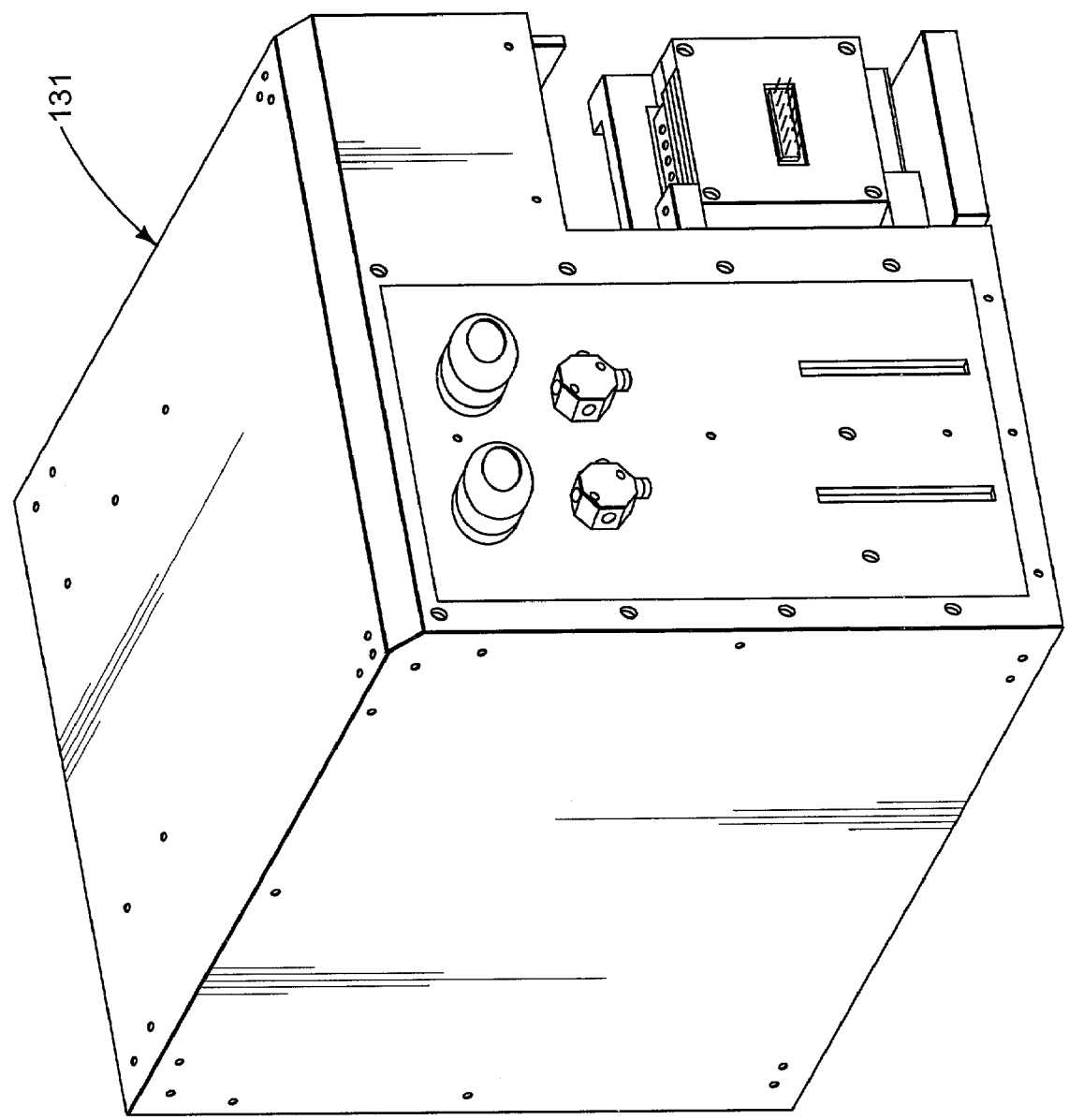
FIG. 25 is an enlarged top perspective view of a fluid control module of the secondary liquid dispensing system of FIG. 21.

Accordingly, the fluid control component 131 is preferably generally provided by the fluid dispensing system illustrated in FIGS. 1–20, and as described in the corresponding description above, and contained in the housing shown in FIG. 25. This system, in accordance with the present invention, provides precision sub-microliter fluid dispension from the non-contact dispense nozzles in the range of one (1) nanoliter to about ten (10) microliters.

Other variations of the fluid control component 131 include designs, it will be appreciated: where the channels are switched by multiple 3-way valves; where the input device is a diaphragm pump; where the input device is an electromechanical piston device actuated by a motor with sub microliter resolution; where the input device is a peristaltic pumping device; where the input device is a vacuum source; where the output device is a piezoelectric device; where the output device is a thermoelectric device such as a bubble jet printing device; and where the output device is a positive displacement device such as a pneumatic device where the output device is a syringe device.

Figure 30:
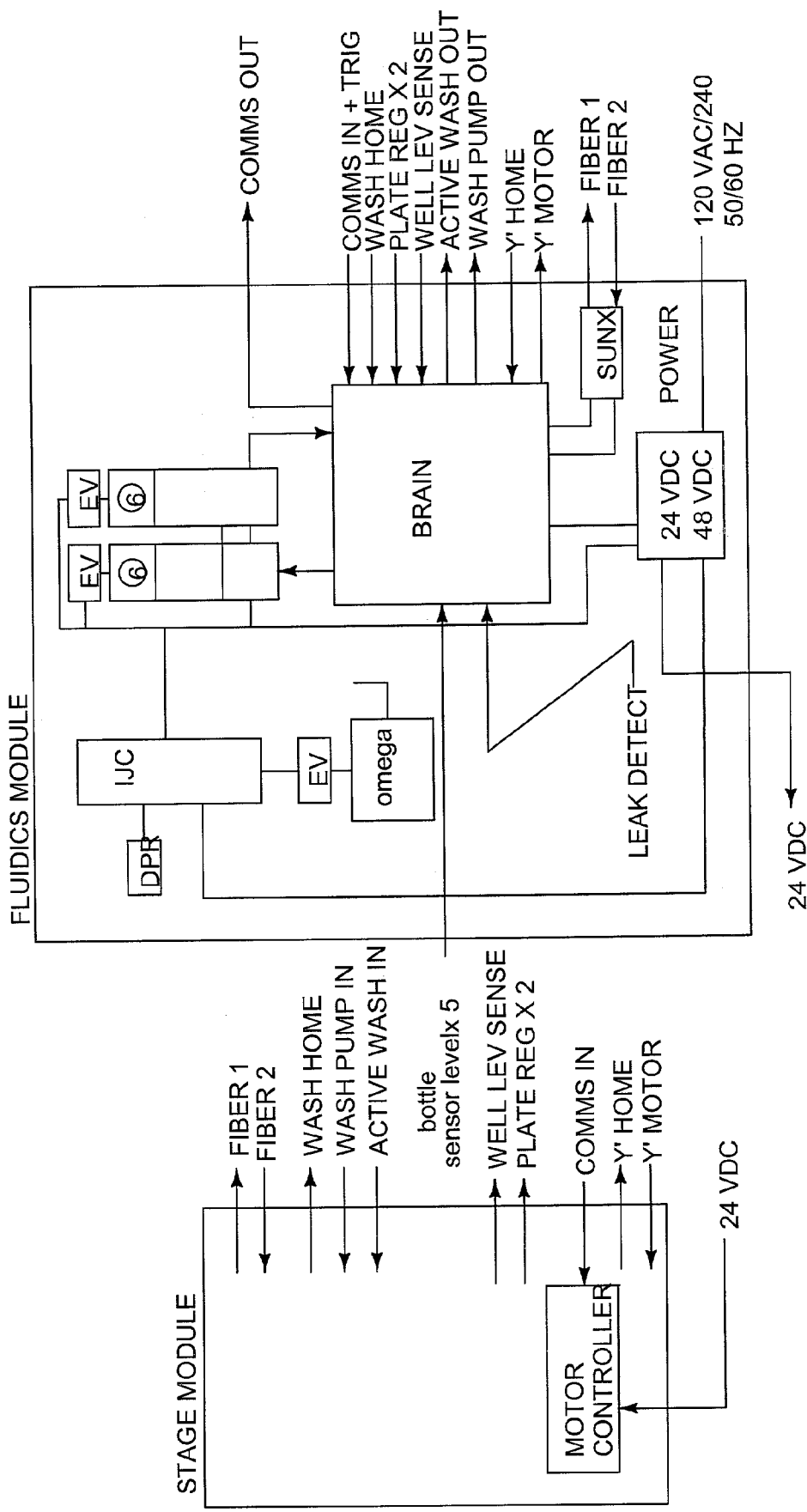
FIG. 30 is a schematic diagram of the secondary fluid dispensing system.

Referring now to FIGS. 26, 28 and 30, the operation interface component 135 is shown which provides standalone or remote operation of the fluid control component 131 and the motion control component 133. More particularly, the interface component 135 operates and integrates the fluid control and motion control components. Incorporated in this chassis are all of the printed circuit boards, connectors, and firmware required to operate the instrument. Software may reside on a host computer independent of the interface component. The primary level liquid handling platforms remotely control this secondary device via a communications channel.

Typically, in accordance with the present invention, these communications channel include a hardware medium and a software protocol. This secondary device has the capability to use RS232 serial ports and can be expanded to include Ethernet, USB and CANBUS hardware mediums. A software driver can be written to support instrument specific software protocols.

The interface component 135 includes a controller PC board (not shown) connected to a host through an RS 232 bus and a standard RS 232 communication wiring protocol. The controller board has embedded firmware that interprets commands from a host application, such as a graphical user interface or an Active-X (OCX) Control, and issues commands to the subcomponents in the fluid control component or the motion control component. Similarly, the controller board may receive commands from third party robotic controller boards. The controller board is further connected to these components through a standard RS 232 serial communication architecture. The subcomponents, the syringe drives, selector valves, hybrid switching valve, ink jet solenoids, motion control component, all have embedded micro processing capabilities that can interpret commands issued to them by the interface control component controller PC board. Variations include systems that rely on the host system to send analog or digital signals to the devices to execute performance of the individual components where none of the sub-components has an embedded microprocessor.

A host computer (not shown) is connected to the interface component 135 through a serial RS 232 connector. Commands are sent to the interface component from the interface component software located on the host computer. Alternatively direct commands may be sent via the RS 232 bus directly to the interface component. Once a command is received by the interface component controller board the command is parsed and distributed by an embedded microprocessor to the subcomponents that are necessary for execution of the command. All subsystems, e.g. the syringe metering component, have associated firmware that operates that individual component. The controller board schedules and communicates with the all the subsystems. Once a command is invoked and completed the controller board can be queried for status.

High and low level commands exist, such that the instrument could be "micro-managed" by low-level step-by-step instructions. These include individually switching valves, moving the XYZ motion control to specific positions, and aspirating and dispensing. Equally, high level commands can be provided to perform a compete operation such as dispensing a specified volume into specified wells.

In accordance with the present invention, a typical cycle involves the aspiration of a source fluid, the dispensing of the fluid onto a destination or multiple destinations, and the washing of, or movement of the nozzle array back to a non-interfering position, such as the "parked" or "wash home" position shown in FIGS. 27 and 28. This allows the destination substrate to be replaced in an automated fashion. The nozzle array is located on the motion control component attached to an existing liquid handling workstation such as a Hamilton Micro Lab 4200 liquid handling device (Hamilton Company, Reno, Nev.). The aspirate step is performed by moving the nozzle array to and into a user defined reagent source (e.g., one of the reagent containers 152, 152'), followed by an aspiration (input) metering by the syringe drive subsystem. Once fluid is in the fluid control component, the hybrid switching valve is switched to an output (dispense) position that places the ink jet solenoids in line with the reagent channels. The motion control component, with the appropriate command from the controller board, moves the nozzle array over the first destination position where a command is issued to actuate the ink jet solenoids causing a volume of fluid to exit the nozzles. Depending on the user defined dispense map, the motion control component positions the nozzle array over the required target positions where iterative ink jet actuations take place until the dispense map is complete. At this point the dispense cycle is finished and either a fluid control system wash occurs, with the subsequent positioning of the: nozzle array in or about a wash station, or the motion control component positions the nozzle array in a "parked" position.

In other alternative applications, the secondary liquid handling peripheral can be employed to aspirate sample from a positioned microtiter plate, and then apply the aspirated sample to other test sites in the same or different microtiter plates. For instance, it can be employed to replicate the sample array of one microtiter plate by aspirating sample, and then, using the positioning mechanism to change microtiter plates, replicate the sample array in the new microtiter plate.

In other arrangement, the primary fluid dispensing device of the automated fluid handling system can cooperate with the secondary fluid dispensing device to enable and facilitate the performance of one or more microbiological procedures. For instance, the primary fluid dispensing device can be employed to dispense fluid quantities into the test sites of the micro titer plates greater than one (1) microliter. In another example, the primary fluid dispensing device can be employed to supply reagent fluid into the reagent containers.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A universal liquid handling system to dispense fluids into the test sites of one or more sample carriers comprising:
   an automated primary liquid handling system including:
   a work area having a plurality of discrete work stations for performing lab work;
   a carrier alignment structure at one or more work stations configured to removably receive and secure one sample carrier therein;
   a frame assembly positioned about the work area; and
   a movable support system movably cooperating with the frame assembly to operationally access each discrete work station within the work area, said movable support system further including
   a sample carrier positioning mechanism containing a positioning head to grip, move, and position the one or more sample carriers to and from the respective work station, and into and out of engagement with the respective carrier alignment structure thereof, and
   a primary liquid dispensing device to selectively dispense discrete quantities of fluid, in the range of microliter to milliliter volumes, into the test sites of the one or more sample carriers secured in the respective alignment structure at the respective work station; and
   a removable, self-contained secondary liquid handling peripheral system adapted for retrofittedly placed and used within the work area of the primary liquid handling system at a selected one or more discrete work stations said liquid handling peripheral system containing a base formed and dimensioned to be placed within a footprint of the selected one or more discrete work stations, and including a support platform having respective carrier alignment structure to removably receive and secure a sample carrier therein provided by the sample carrier positioning mechanism said secondary liquid handling peripheral system being operationally independent of the primary liquid handling system and including a secondary liquid dispensing device having one or more non-contact dispense nozzles to selectively non-contact dispense discrete quantities of fluid, in the range nanoliter to microliter volumes, into the test sites of the sample carrier positioned therein,
   wherein a sample carrier is positioned on the support platform and is operationally accessible by both the primary liquid dispensing device and the secondary liquid dispensing device.

2. The universal liquid handling system according to claim 1, wherein
   said secondary liquid dispensing device is adapted to dispense fluids in the range of about one (1) nanoliter to about ten (10) microliters.

3. The universal liquid handling system according to claim 2, wherein
   said primary liquid dispensing device is adapted to dispense fluids in the range of about one (1) microliter to about ten (10) milliliters.

4. The universal liquid handling system according to claim 1, wherein
   said carrier alignment structure of said secondary liquid handling peripheral system is adapted to receive and secure standardized sample carrier microtiter-plates.

5. The universal liquid handling system according to claim 2, wherein
   at least one work station conforms to a Society of Bimolecular Screening (SBS) lab ware site.

6. The universal liquid handling system according to claim 3, wherein
   said carrier alignment structure is adapted to conform with an SBS standard microtiter-plate lab ware site.

7. The universal liquid handling system according to claim 6, further including:
   mounting hardware enabling removable mounting of said peripheral system to an SBS standard lab ware site.

8. The universal liquid handling system according to claim 1, wherein
   said primary liquid dispensing device is a contact-type liquid dispenser.

9. The universal liquid handling system according to claim 1, wherein
   said secondary liquid dispensing device includes a fluid control component to aspirate fluids therein, and dispense fluids from the one or more non-contact dispense nozzles, and a motion control component for positioning of the one or more non-contact dispense nozzles to selectively dispense the aspirated fluids into a targeted test site of a mounted sample carrier.

10. The universal liquid handling system according to claim 9, wherein
    said secondary liquid dispensing device further includes an operation interface component coupled between the fluid control component and the motion control component for stand-alone or remote control operation of the fluid control component and the motion control component.

11. The universal liquid handling system according to claim 9, wherein
    said fluid control component includes a hybrid valve apparatus that enables fluid aspiration, fluid dispensing and fluid switching to transfer fluid from a fluid reservoir and through the one or more non-contact dispense nozzles to the targeted test sites.

12. The universal liquid handling system according to claim 11, wherein said fluid control component includes an aspiration source in fluid communication with a first aspiration port of the hybrid valve apparatus, and a dispensing source in fluid communication with a first dispensing port of the hybrid valve apparatus, and said hybrid valve apparatus including a valve assembly movable between an aspiration condition and a dispensing condition, and a manifold device providing a fluid aspiration conduit in fluid communication with the aspiration source through said first aspiration port thereof, and a second aspiration port in selective fluid communication with the valve assembly to selectively aspirate a liquid slug from the fluid reservoir into a discrete sample path of the valve apparatus when the valve assembly is in the aspiration condition, said manifold device further providing a fluid dispensing conduit in fluid communication with the dispensing source through said first dispensing port thereof, and a second dispensing port in selective fluid communication with the valve assembly to selectively dispense at least one droplet of the liquid slug from the sample path when the valve assembly is in the dispensing condition, wherein, in the aspiration condition, said sample path is out of fluid communication with the dispensing source and, in the dispensing condition, said sample path is out of fluid communication with the aspiration source.

13. The universal liquid handling system according to claim 12, wherein said manifold device includes a stator face containing the second aspiration port and the second dispensing port, and said valve assembly includes a valve body having a contact face slideably contacting the stator face at a stator-contact interface for sliding sealed contact between the aspiration condition, fluidly coupling the second aspiration port to the sample path, and the dispensing condition, fluidly coupling the second dispensing port to the sample path.

14. The universal liquid handling system according to claim 13, wherein said contact face of the valve body includes an aspiration channel, fluidly coupling the second aspiration port to the sample path through the aspiration channel, in the aspiration condition, and a dispensing channel, fluidly coupling the second dispensing port to the sample path through the dispensing channel, in the dispensing condition.

15. The universal liquid handling system according to claim 14, wherein at least one of said valve body and said manifold device is rotatable about a rotation axis extending substantially perpendicular to the stator-contact interface to rotate said contact face, said aspiration channel and said dispensing channel relative to the stator face between the aspiration condition and the dispensing condition.

16. The universal liquid handling system according to claim 15, wherein said dispensing channel and said aspiration channel extend in a direction substantially radially about said rotational axis.

17. The universal liquid handling system according to claim 16, wherein said manifold device includes a primary passage having an upper communication port terminating at the stator face, and an opposite end in fluid communication with a respective nozzle having a dispensing orifice configured to dispense said droplet, and a source conduit having an upper communication opening terminating at the stator face, and an opposite end in fluid communication with the reservoir.

18. The universal liquid handling system according to claim 17, wherein said contact face of the valve body includes a sample channel forming at least a portion of the sample path, said sample channel fluidly coupling the second aspiration port of the aspiration conduit to the upper communication opening of the source conduit, in the aspiration condition, and fluidly coupling the second dispensing port of the dispensing conduit to the upper communication port of the primary passage, in the dispensing condition.

19. The universal liquid handling system according to claim 18, wherein said manifold device includes a flush passage having an upper flush port terminating at the stator face, and an opposite end in fluid communication with a flush source, and said contact face of the valve body includes a flush channel fluidly coupling the flush port of the flush passage to the upper communication port of the primary passage, in the aspiration condition, to flush said respective nozzle, and fluidly coupling the flush port to the upper communication opening of the source conduit, in the dispensing condition.

20. The universal liquid handling system according to claim 9, wherein said motion control component includes a base member supporting said support platform thereon such that when said base member is strategically positioned at a respective discrete work station, said respective carrier alignment structure removably receives and secures the sample carrier therein.

21. The universal liquid handling system according to claim 20, wherein said motion control component further includes a motion controller device, supporting the one or more liquid dispense nozzles, and positioning the same for said selective dispense of the discrete quantities of fluid into the targeted test site.

22. The universal liquid handling system according to claim 21, wherein said motion controller device includes a control post configured for movement along a three-axis X-Y-Z Cartesian coordinate system.

23. The universal liquid handling system according to claim 22, wherein said motion controller device includes a rail system and stepper motor device which cooperate with the control post to move the one or more nozzles independently along the X, Y and X axis.

24. The universal liquid handling system according to claim 23, wherein the carrier alignment structure of said secondary liquid handling peripheral system and the support platform of the secondary liquid handling peripheral system cooperate to provide a Society of Bimolecular Screening (SBS) standard microtiter-plate lab ware site.

25. The universal liquid handling system according to claim 24, wherein each of the work stations conform to a Society of Bimolecular Screening (SBS) lab ware site, the secondary liquid handling peripheral system includes mounting hardware enabling removable mounting of said peripheral system to an SBS standard lab ware site.

26. The universal liquid handling system according to claim 22, wherein said motion controller device is one of linear motion control based, servo control based and pneumatic control based.

27. The universal liquid handling system according to claim 22, wherein said one or more nozzles are provided by a plurality of non-contact dispense nozzles each having one end fluidly coupled to the fluid control component and an opposite end terminating at a dispensing orifice configured to dispense said droplet.

28. The universal liquid handling system according to claim 27, wherein said fluid control component includes a hybrid valve apparatus fluidly coupled between one or more fluid reservoirs and the one ends of the plurality of the non-contact dispense nozzles to enable fluid aspiration, fluid dispensing and fluid switching to transfer fluid from selected fluid reservoir and through selected dispense nozzles to the targeted test sites.

29. The universal liquid handling system according to claim 12, wherein said dispensing source includes drop-on demand valving.

30. The universal liquid handling system according to claim 29, further including said drop-on demand valving is one of a thermal ink-jet valve, a solenoid ink-jet valve, a piezoelectric ink-jet valve, and a pneumatic pilot valve.

31. The universal liquid handling system according to claim 12, wherein said dispensing source includes one of a syringe-type metering device, a piezoelectric-type metering device, a thermoelectric-type metering device and a positive displacement-type metering device.

32. The universal liquid handling system according to claim 31, wherein said syringe-type metering device includes a multiple selector valve connecting a single syringe-type metering device to multiple fluid paths.

33. The universal liquid handling system according to claim 32, wherein said aspiration source includes one of a diaphragm pump-type metering device, an electromechanical piston-type metering device actuated by a motor with sub microliter resolution, a vacuum source-type metering device and a peristaltic pump-type metering device.

34. The universal liquid handling system according to claim 12, wherein said aspiration source includes a plurality of aspiration actuators, and said dispensing source includes a plurality of dispensing actuators to transfer aspirated fluid from one or more fluid reservoirs to test sites of said sample carrier positioned on the secondary liquid handling peripheral system, and said manifold device including a plurality of fluid aspiration conduits each having a first aspiration port in fluid communication with a corresponding aspiration actuator, and a second aspiration port terminating at the stator face for selective fluid communication with the valve assembly to selectively aspirate a respective liquid slug from a corresponding fluid reservoir into discrete sample paths when the valve assembly is in the aspiration condition, said manifold body further defining a plurality of fluid dispensing conduits each having a respective first dispensing port in fluid communication with a corresponding dispensing actuator, and a second dispensing port terminating at the stator face for selective fluid communication with the valve assembly to selectively dispense at least one droplet of the corresponding liquid slug from the corresponding sample path when the valve assembly is in the dispensing condition wherein, in the aspiration condition, each respective sample path is out of fluid communication with the respective dispensing actuator and, in the dispensing condition, each respective sample path is out of fluid communication with the respective aspiration actuator.

* * * * *

UNITED STATES PATENT AND TRADEMARK OFFICE
CERTIFICATE OF CORRECTION

| | | |
|---|---|---|
| PATENT NO. | : 7,135,146 B2 | Page 1 of 1 |
| APPLICATION NO. | : 10/237916 | |
| DATED | : November 14, 2006 | |
| INVENTOR(S) | : Johnson et al. | |

It is certified that error appears in the above-identified patent and that said Letters Patent is hereby corrected as shown below:

Column 1, line 8, change "09/689,5548" to --09/689,548--.

Signed and Sealed this

Seventh Day of August, 2007

JON W. DUDAS
*Director of the United States Patent and Trademark Office*